United States Patent
Gupta et al.

(10) Patent No.: US 8,227,426 B2
(45) Date of Patent: Jul. 24, 2012

(54) CHIRAL COMPLEXES OF ASCORBIC ACID WITH NATURAL ANTIOXIDANT AND ANTI-INFLAMMATORY KETONES INCLUDING ALOE, CITRUS, GINGER, AND MANGO FOR SKIN AND HAIR CARE

(75) Inventors: Shyam K Gupta, Scottsdale, AZ (US); Linda Walker, Cardiff, CA (US)

(73) Assignee: Island Kinetics Inc., Chandler, AZ (US)

( * ) Notice: Subject to any disclaimer, the term of this patent is extended or adjusted under 35 U.S.C. 154(b) by 43 days.

(21) Appl. No.: 12/947,314

(22) Filed: Nov. 16, 2010

(65) Prior Publication Data

US 2011/0059907 A1  Mar. 10, 2011

Related U.S. Application Data

(63) Continuation-in-part of application No. 12/139,659, filed on Jun. 16, 2008, now abandoned.

(51) Int. Cl.
  *A01N 43/04* (2006.01)
  *A61K 8/73* (2006.01)
(52) U.S. Cl. .................... 514/23; 424/70.13
(58) Field of Classification Search .............. None
  See application file for complete search history.

(56) References Cited

U.S. PATENT DOCUMENTS

| 4,287,205 A * | 9/1981 | Szent-Gyorgyi et al. ..... 514/465 |
| 6,998,111 B2 | 2/2006 | Klee |
| 2008/0255228 A1 | 10/2008 | Gupta |

* cited by examiner

*Primary Examiner* — Paul Dickinson

(57) ABSTRACT

This invention relates to certain complexes of ascorbic acid and its derivatives with certain natural antioxidant and anti-inflammatory ketones for topical or oral application; said complexes having general chemical formula (I), its isomers, and salts thereof, including their optically active or racemic forms. This invention also relates to a method of treatment of skin condition, including dark skin, age spots, acne, inflammation, loss of cellular antioxidants, collagen loss with aging, loss of skin pliability, loss of skin suppleness, skin wrinkles, oxidation, damage from radiation, malfunction of matrix metalloproteases, malfunction of tyrosinases, damage from free radicals, photo-damage, nutritional deficiency, and combinations thereof;

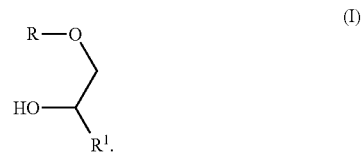

13 Claims, 2 Drawing Sheets

Reversion of A Furo[3,4-d][1,3]dioxol-4-[6H]one into Ascorbic Acid and Ketone

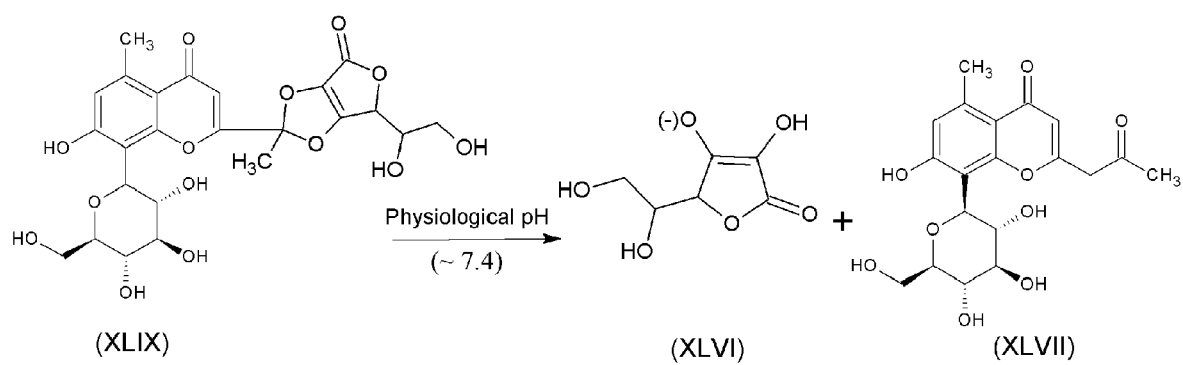
Fig. 1. Reversion of A Furo[3,4-d][1,3]dioxol-4-[6H]one into Ascorbic Acid and Ketone

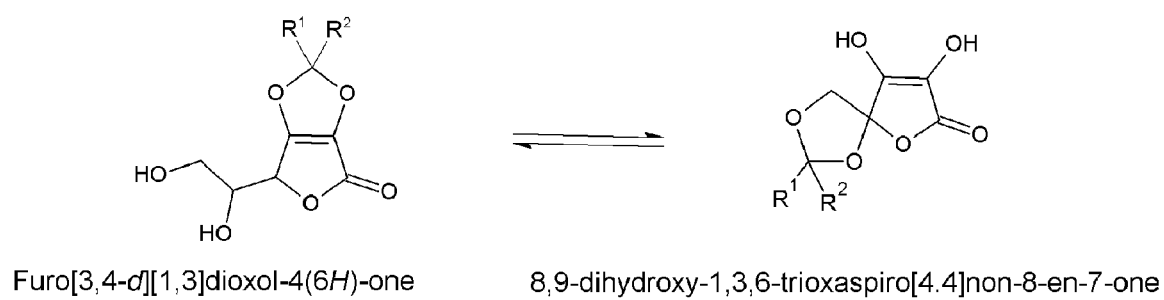
Fig. 2. Isomerization of Furo[3,4-d][1,3]dioxol-4[6H]one

CHIRAL COMPLEXES OF ASCORBIC ACID WITH NATURAL ANTIOXIDANT AND ANTI-INFLAMMATORY KETONES INCLUDING ALOE, CITRUS, GINGER, AND MANGO FOR SKIN AND HAIR CARE

The present invention is a continuation-in-part of U.S. patent application Ser. No. 12/139,659 (filed Jun. 16, 2008) now abandoned.

BACKGROUND OF THE INVENTION

The incorporation of botanical antioxidants in cosmetic products is gaining popularity due to anti aging and other skin tone enhancement benefits. Cosmetic products formulated with familiar antioxidants such as ascorbic acid, aloe, vitamin E, Coenzyme Q10, α-lipoic acid, and soy isoflavones have appeared in the marketplace with skin and hair beneficial claims. The design of a topical antioxidant product offers challenges: A wide spectrum antioxidant product should control cellular oxidation resulting from biochemical mechanisms including oxygen, free radicals, UV, atmospheric pollutants, oxidative enzymes, catabolic oxidation, and chemical oxidation.

A combination of antioxidants is usually more effective than a single antioxidant on an equal weight basis due to antioxidant cascade mechanism. The combination of antioxidant ingredients should be selected from different chemical classes to control cellular oxidation resulting from various biochemical mechanisms. The total quantity of antioxidants should be balanced carefully, as an excessive amount of antioxidants may have an opposite, pro-oxidant effect resulting in poor stability and performance of the product. This necessitates use of multiple antioxidants in a composition to provide optimized skin and hair care benefits.

It would thus be highly advantageous to combine two or more of such antioxidants into a new chemical entity that would provide synergistically enhanced benefits of the individual components. Well-known antioxidants such as aloesin, aloin, phloridzin, phloretin, curcumin, tetrahydrocurcumin, hesperidin, mangostin, mangiferin, and hypericin contain a keto group in their chemical structure. Antioxidants that are aldo or keto hydroxyacids, such as ascorbic acid and its derivatives, possess one or more vicinal diol groups that can be chemically reactive with a keto group.

The present invention discloses antioxidant agents that are derived from two different antioxidant reactants, one of which contains a keto group and the other a vicinal diol. The vicinal diol is converted to a dioxol or furan derivative via this chemical process, which results in surprisingly enhanced skin permeability of said antioxidant agent over said vicinal diol or keto antioxidant reactants. The use of a single said antioxidant agent eliminates the use of multiple antioxidants in a composition, yet imparts superior overall antioxidant treatment for skin and/or hair.

The present invention relates to complexes (hereinafter referred to as "complex", or "complexes", or "ascorbyl complex") of certain aldo or keto hydroxyacids, such as ascorbic acid and its derivatives, and certain commercially well known antioxidants having a keto group; said complexes, [Furo[3,4-d][1,3]dioxol-4(6H)-ones] and/or its structural isomer, 3,4-dihydroxyfuran-2(5H)-one, both of which having various chiral, meso, racemic, and other isomeric forms.

This invention also relates to a method of treatment of a condition, such as a skin or a hair condition and the cause for such condition, such as nutritional deficiency, including dark skin, age spots, acne, inflammation, loss of cellular antioxidants, collagen loss with aging, loss of skin pliability, loss of skin suppleness, skin wrinkles, oxidation, damage from radiation, malfunction of matrix metalloproteases, malfunction of tyrosinases, damage from free radicals, damage from UV, hair loss, hair graying, nutritional deficiency, and combinations thereof.

DESCRIPTION OF THE RELATED ART

The acetal and ketal derivatives of keto hydroxyacids with aliphatic aldehydes and ketones are known in the prior art.

Bharucha et al. (U.S. Pat. No. 4,153,613), Satoh et al. (U.S. Pat. No. 5,194,445), and Terao et al. (U.S. Pat. Nos. 4,780,549 and 4,959,362) disclose the reaction of ascorbic acid (IV) with certain aliphatic aldehydes or ketones to form the corresponding acetals or ketals, 8,9-dihydroxy-1,3,6-trioxaspiro[4.4]non-8-en-7-ones.

Klee et al. (U.S. Pat. No. 6,998,111) disclose the most pertinent prior art.

The topical application of ascorbic and other hydroxy acids and their various derivatives, such as salts and esters, for the treatment of skin and hair condition has been well practiced in the prior art. However, the poor stability of ascorbic acid in topical compositions, especially those that contain water, is also well known. There have been numerous attempts to provide stable ascorbic acid derivatives. However, most of such derivatives have received poor consumer application due to a combination of several drawbacks, which include their commercial unavailability, high cost, and reduced antioxidant, collagen boosting and skin whitening benefits. Some of such prior art examples are noted below, the detailed perusal of which would serve to illustrate the point made above.

Anderson et al. (U.S. patent application Ser. No. 20060189579) disclose stabilization of ascorbyl phosphate by coating with a lipid.

Buononato et al. (U.S. patent application Ser. No. 20040157800) disclose L-carnitine and lower alkanoyl L-carnitine ascorbyl derivatives and topically applicable cosmetic compositions comprising same as active ingredients.

Kutney et al. (U.S. patent application Ser. No. 20030232797) disclose certain steroidal derivatives of ascorbic acid and use thereof in treating or preventing various conditions, diseases, and disorders.

Perricone et al. (U.S. Pat. No. 6,162,419) disclose certain stabilized ascorbyl compositions.

Streicher et al. (U.S. Pat. No. 6,143,906) disclose certain ascorbyl sorbates.

Hamano et al. (U.S. Pat. No. 5,879,692) disclose tocopheryl ascorbyl phosphate-cyclodextrin clathrates, and topical dermal compositions containing said clathrates.

Ptchelintsev (U.S. Pat. Nos. 5,780,504; 5,607,968) discloses certain topical alkyl-2-O-L-ascorbyl-phosphates.

Kaiser et al (U.S. Pat. No. 5,420,302) disclose preparation of stable calcium L-ascorbate 2-phosphate.

Pauling et al. (U.S. Pat. No. 5,210,220) disclose certain ascorbyl phosphates as stabilized ascorbic acid derivatives.

McAuliffe et al. (EP 1,833,881) disclose certain ester derivatives of ascorbic acid and 2-keto acids.

Shibayama et al. (EP 1,666,484) disclose certain stable esters of ascorbyl phosphate, which are useful as skin whitening agents.

Gupta (U.S. patent application Ser. No. 20040034094) discloses certain stabilized compositions of ascorbic acid.

Marion (EP 1,637,124) discloses a combination of water-soluble ascorbic acid derivative and a porous polyamide for skin care compositions.

Vromen (EP 1,688,130) discloses certain stable preparations of ascorbic acid that contain micronized ascorbic acid in an anhydrous base.

Mathur (U.S. Pat. No. 4,096,240) discloses niacinamide ascorbate for skin whitening application.

Meisner (U.S. patent application Ser. No. 20080125395) discloses a topical preparation of ascorbic acid.

Roomi et al. (U.S. Pat. No. 7,230,124) disclose certain derivatives of ascorbic acid with lysine.

Ruhe (U.S. Pat. No. 6,602,906) discloses ascorbic acid ketal of acetone for topical compositions.

Castiel et al. (U.S. patent application Ser. No. 20020042380) disclose 2,3-substituted ascorbic acid derivatives for skin care.

Zimmermann et al. (U.S. patent application Ser. No. 20080124409, and references cited therein) disclose topical skin compositions, their preparation, and their use that contain ascorbic acid and its derivatives.

It is worthy of note that none of prior art methods above disclose Furo[3,4-d][1,3]dioxol-4(6H)-ones of the present invention.

BRIEF DESCRIPTION OF THE SEVERAL VIEWS OF THE DRAWINGS

[FIG. 1]. Reversion of A Furo[3,4-d][1,3]dioxol-4(6H)-one into Ascorbic Acid and Ketone.

[FIG. 2]. Isomerization of Furo[3,4-d][1,3]dioxol-4(6H)-ones.

DETAILED DESCRIPTION

Certain aldo or keto hydroxyacids, such as ascorbic acid and its derivatives, have been well studied in the prior art. Ascorbic acid itself has found applications as a vitamin, skin-whitening agent, collagen booster, and a cellular antioxidant. A vast number of other antioxidants are also known in the prior art. It has been common in the prior art to use said antioxidants in oral or topical formulations in a combination form to provide optimized antioxidant benefits. It is also well known that an excessive use of an antioxidant or a mixture of antioxidants can cause pro-oxidant affect. Exactly what determines the excessive combination for such pro-oxidant affect is not well understood. However, a number of said antioxidants contain an aldo or a keto group.

The present invention discloses certain chiral complexes of aldo and keto hydroxyacids with antioxidant ketones; said complexes, [Furo[3,4-d][1,3]dioxol-4(6H)-ones], having general chemical formula (I), and, wherein said "complexes" having various chiral, meso, or racemic forms and salts thereof for oral or topical application:

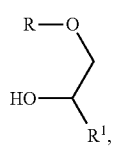

(I)

wherein;
R is selected from H, $C^1$-$C^{20}$ alkyl, aralkyl, and $C^1$-$C^{20}$ acyl; and
$R^1$ is selected from the group consisting of:

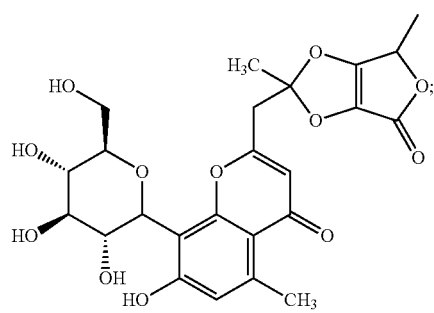

(II)

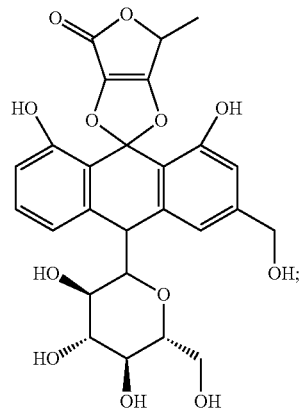

(III)

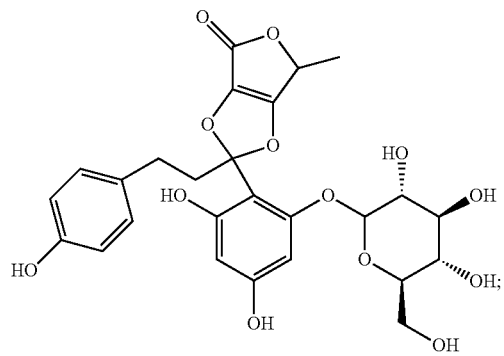

(IV)

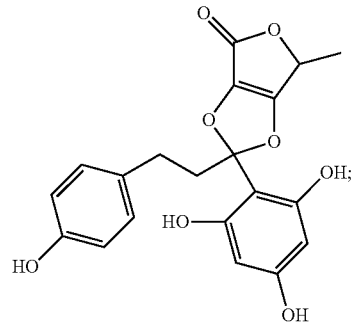

(V)

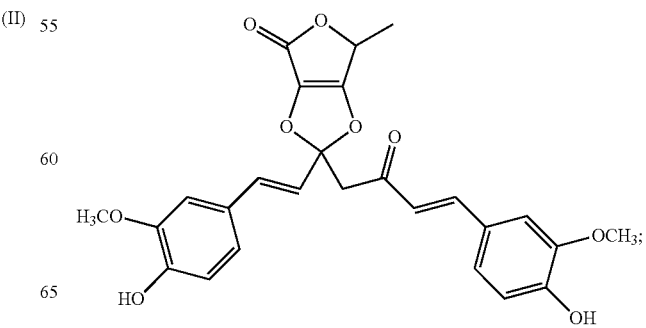

(VI)

(VII)
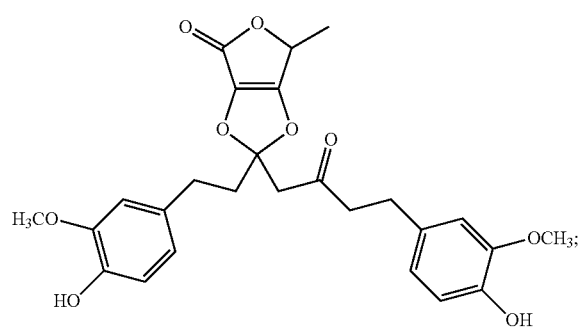
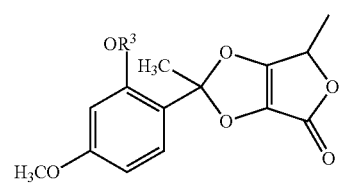
wherein,
R³=H (VIII),
R³=β-D-Glucose (IX);
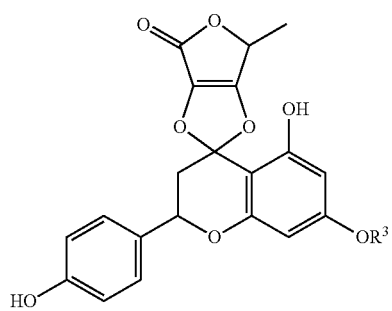
wherein,
R³=H (X),
R³=β-D-Glucose (XI);
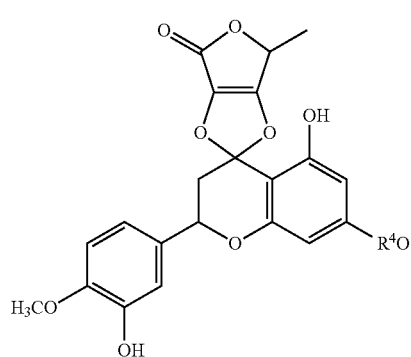
wherein,
R⁴=H (XII),
R⁴=Saccharide (XIII);
(XIV)
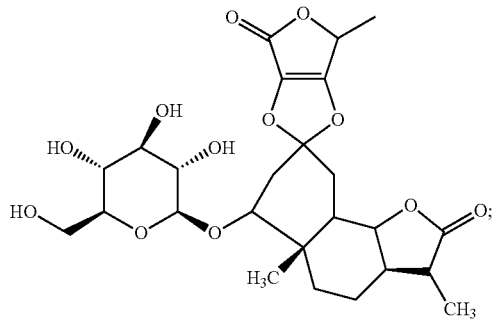
(XV)
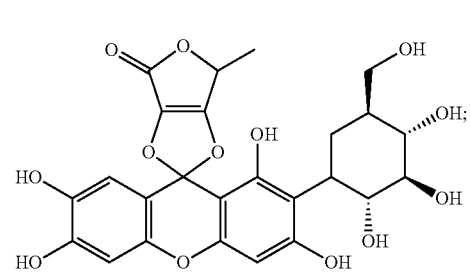
(XVI)
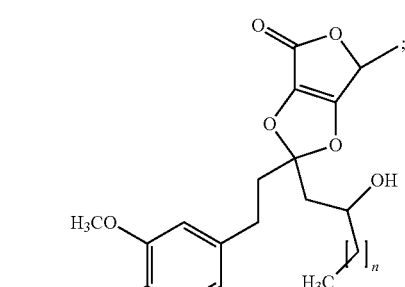
wherein, n=1, 2, 3, 4, 6, 8, 10
(XVII)
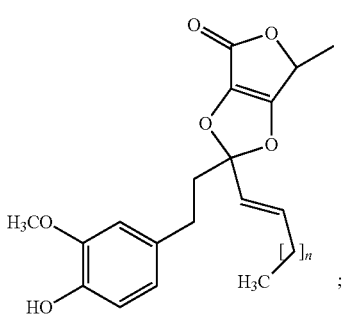
wherein, n=; 3, 4, 5, 6, 8, 10
(XVIII)
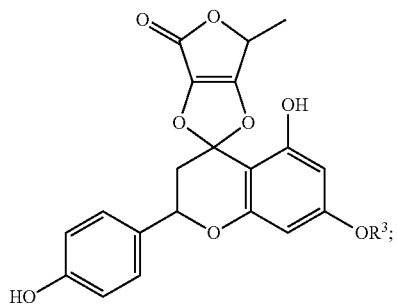

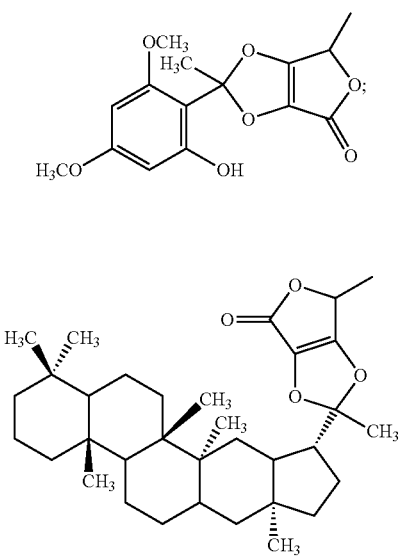
(XIX)
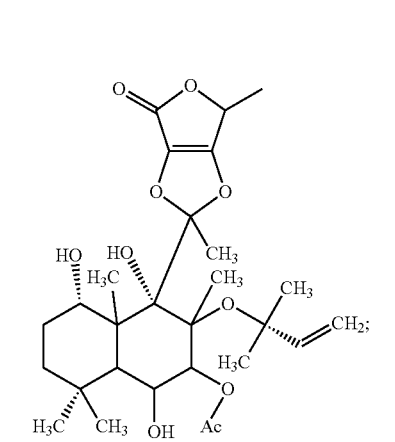
(XX)
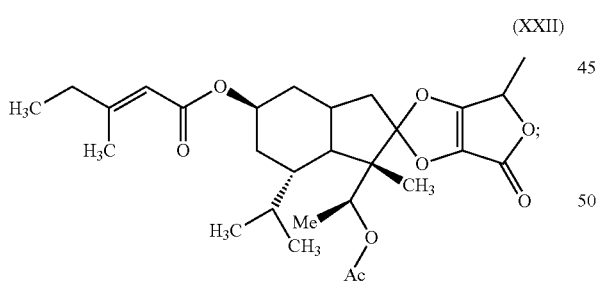
(XXI)
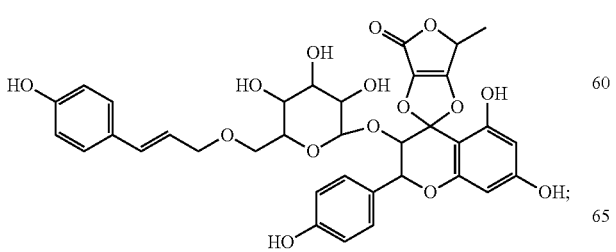
(XXII)
(XXIII)
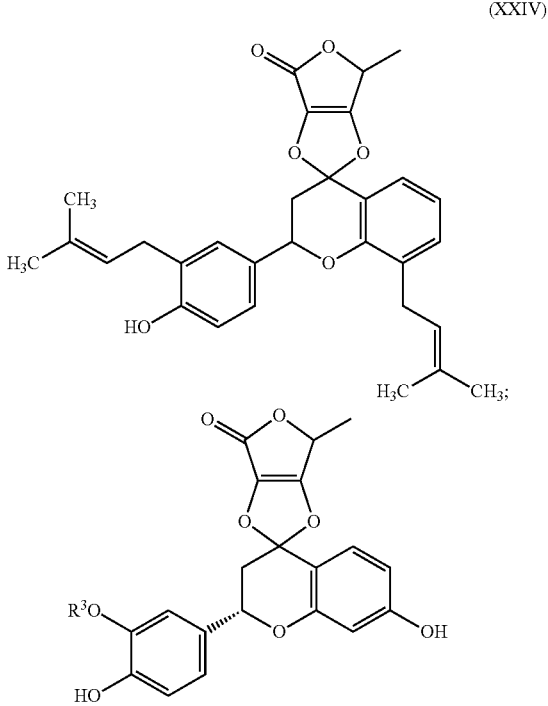
(XXIV)
wherein,
R³=H (XXV),
R³=β-D-Glucose (XXVI);
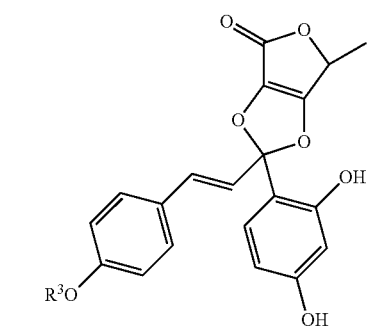
wherein,
R³=H (XXVII)
R³=β-D-Glucose (XXVIII);
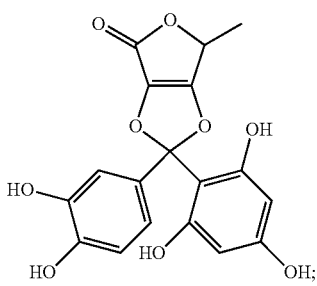
(XXIX)

wherein,
R=H (XXXV),
R=OH (XXXVI);

wherein,
R=Me (XXXI),
R=CH$_2$OH (XXXII);

wherein,
R$^1$=H, R$^2$=CH$_3$ (XXXVII)
R$^1$=H, R$^2$=CH$_2$OH (XXXVIII)
R$^1$=OH, R$^2$=CH$_3$ (XXXIX);

(XLIV)

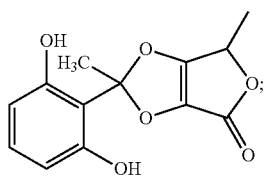

(XLV)

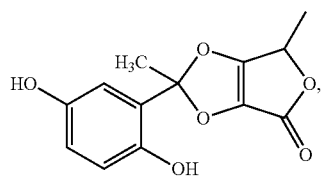

and combinations thereof.

In the process of the present invention, the reaction of ascorbic acid (XLVI) with an antioxidant, anti-inflammatory ketone, for example aloesin (XLVII), provides the complex, 2-[8,9-dihydroxy-2-methyl-7-oxo-1,3,6-trioxaspiro[4,4] non-8-en-2-yl)methyl]-7-hydroxy-5-methyl-8-[(3R,4R,5S, 6R)-3,4,5-trihydroxy-6-(hydroxymethyl)tetrahydro-2H-pyran-2-yl]-4H-chromen-4-one of formula (XLVIII) and its isomer, 8-(2R,3S,4R,5S)-2-(hydroxymethyl)tetrahydro-2H-pyran-3,4,5-triol-7-hydroxy-2-{[4-hydroxy-4-(hydroxymethyl)-2-methyl-6-oxo-4,6-dihydrofuro[3,4-d][1,3]dioxol-2-yl]methyl}-5-methyl-4H-chromen-4-one, of formula (XLIX);

The chiral compounds of the present invention are further characterized by their optical rotation and optical rotatory dispersion (ORD) data.

Additional examples of said antioxidant and anti-inflammatory ketones from botanical sources include;

Aloe (Aloe vera or Aloe barbedensis):

(L)

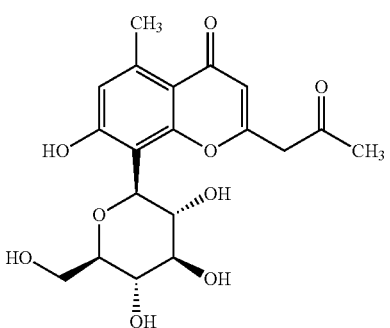

Aloesin (L)

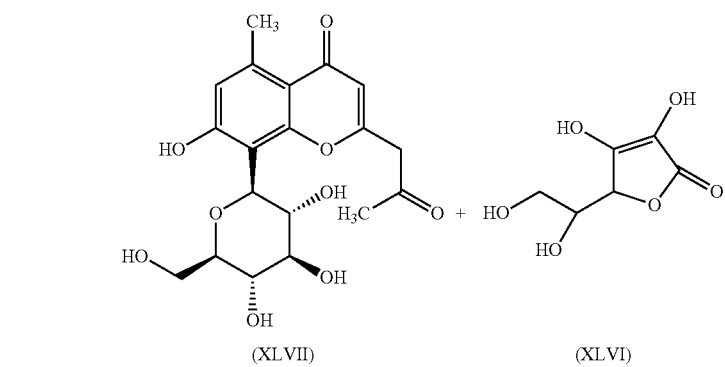

(XLVII)                    (XLVI)

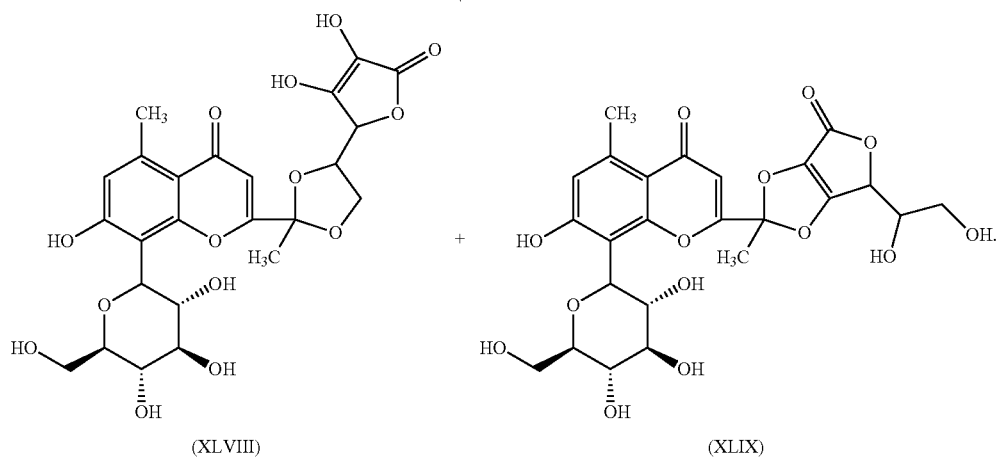

(XLVIII)                              (XLIX)

-continued
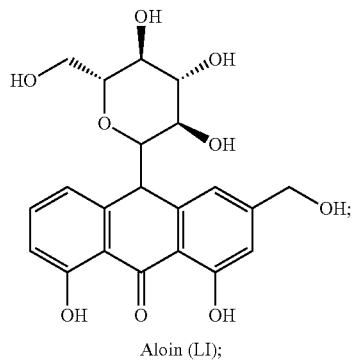
Aloin (LI);
Apple (*Pyrus malus*):
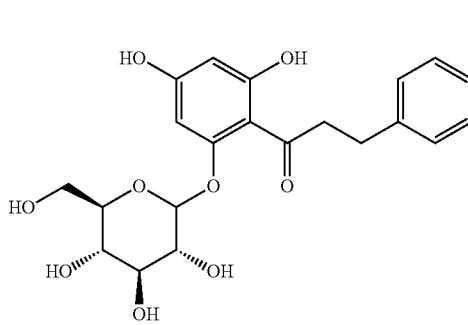
Phloridzin (LII)
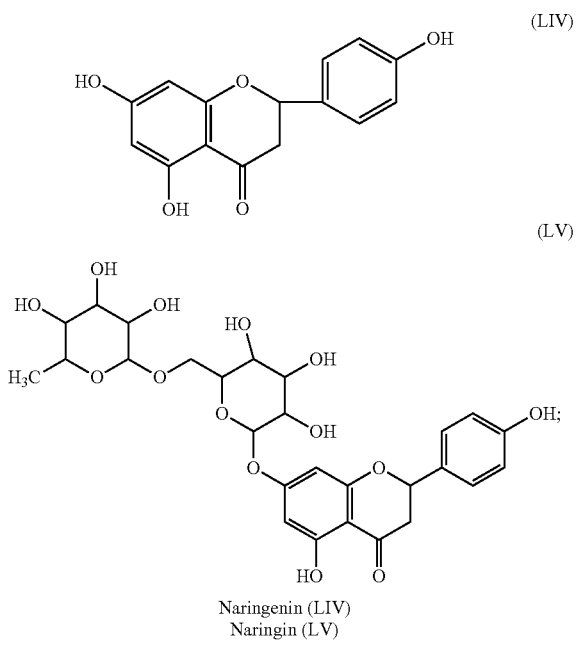
Phloretin (LIII)
Citrus (*Citrus aurantium, Citrus paradisi*):
Naringenin (LIV)
Naringin (LV)
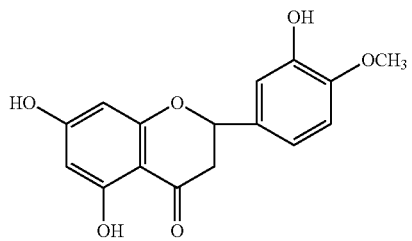
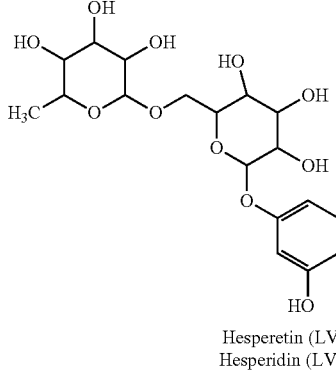
Hesperetin (LVI)
Hesperidin (LVII)
Coleus Root (*Coleus forskohlii*):
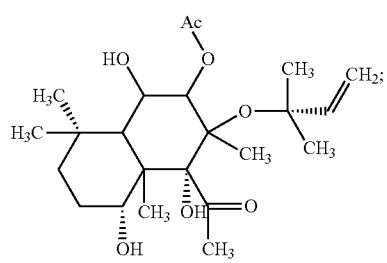
Forskohlin (LVIII)
Coltsfoot (*Tussilago farfara*):
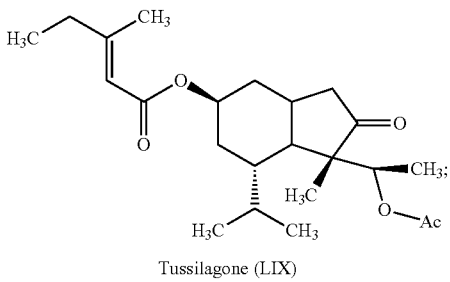
Tussilagone (LIX)
Dandelion (*Taraxacum officinale*):
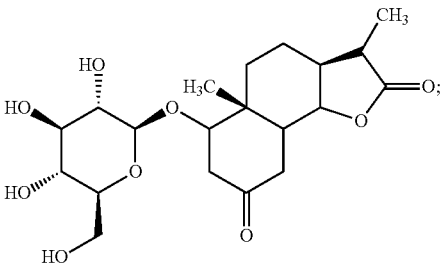
Taraxacolide (LX)

Ginger (*Zingiber officinale*):

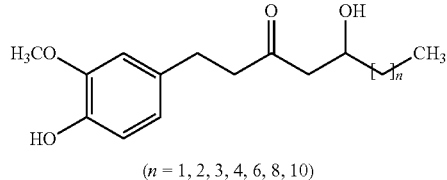

(n = 1, 2, 3, 4, 6, 8, 10)

(LXI)

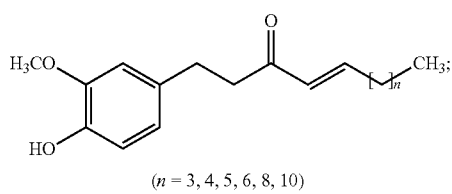

(n = 3, 4, 5, 6, 8, 10)

Gingerols (LXI)

Shogaols (LXII)

Japanese Pepper (*Zanthoxylum piperitum*):

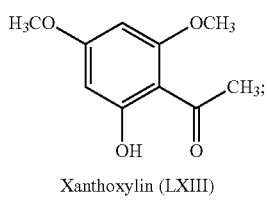

Xanthoxylin (LXIII)

Licorice Root (*Glycyrrhiza glabra*):

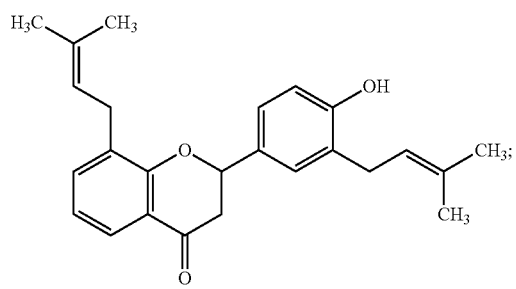

Glabrol (LXIV)

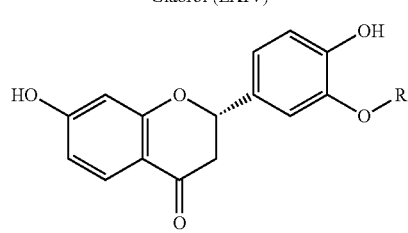

Liquiritin R = —O-Glucosyl (LXV)
Liquiritigenin R = H (LXVI);

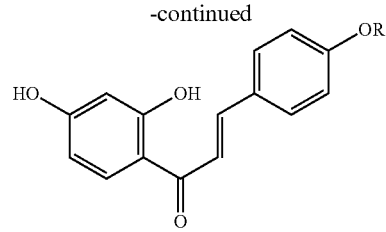

Isoliquiritin R = —O-Glucosyl (LXVII)
Isoliquiritigenin R = H (LXVIII);

Linden Flower (*Tilia officinal's*):

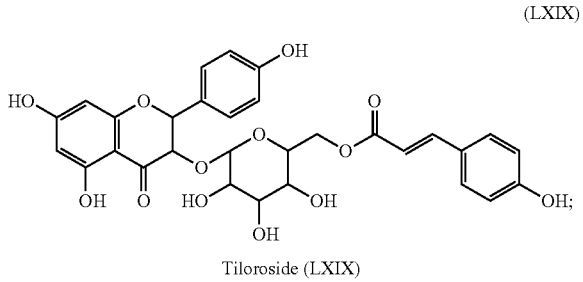

Tiloroside (LXIX)

Maiden Hair Fern (*Adiantun capillusveneris*):

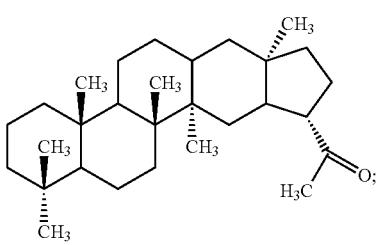

Adiantone (LXX)

Mango (*Mangifera indica*):

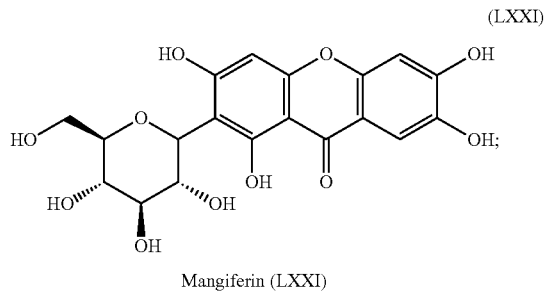

Mangiferin (LXXI)

Mangosteen (*Garcinia mangostana*):

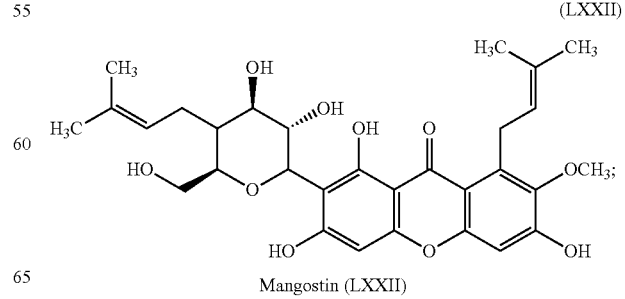

Mangostin (LXXII)

Mulberry (*Morus alba*):

Maclurin (LXXIII)

Peony (*Paeonia suffruticosa*):

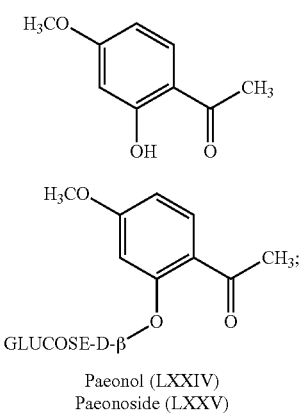

Paeonol (LXXIV)
Paeonoside (LXXV)

Salvia (*Salviae miltiorrhizae*):

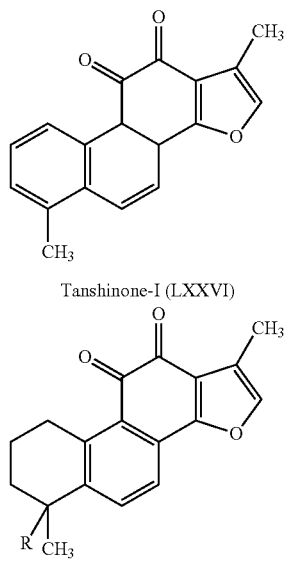

Tanshinone-I (LXXVI)

Tanshinone-IIA R = Me (LXXVII)
Tanshinone-IIB R = CH$_2$OH (LXXVIII);

Sophora (*Sophora flavescens*):

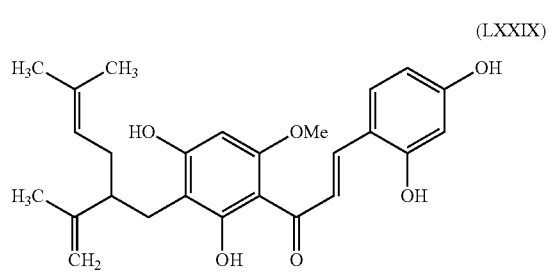

-continued

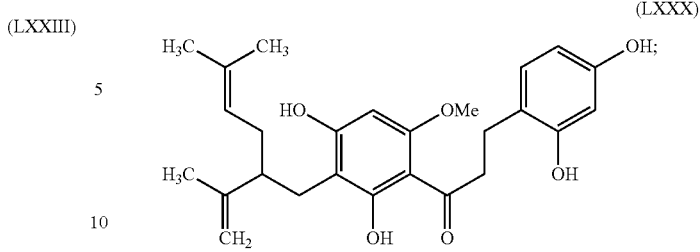

Kuraridin (LXXIX)
Kuraridinol (LXXX)

Tallow Tree (*Sapium sebiferum*):

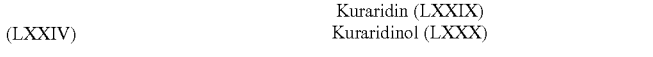

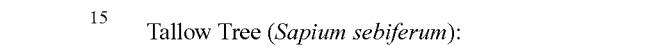

R = -β-D-Xylopyranosyl-(1,6)-β-D-Glucopyranoside (LXXXI);
Xanthoxylin Xylosylglucoside (LXXXI)

Turmeric (*Curcuma longa*):

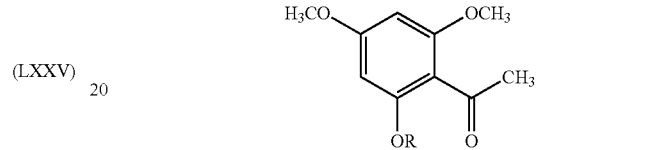

CURCUMIN

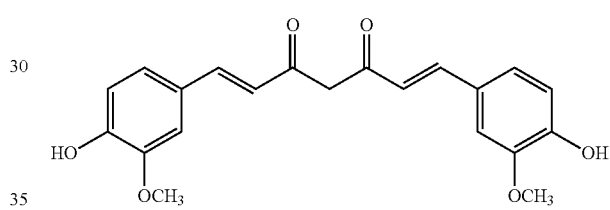

DEMETHOXYCURCUMIN

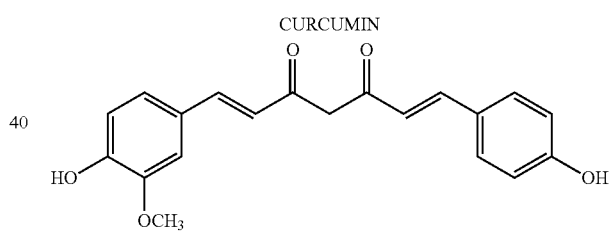

BISDEMETHOXYCURCUMIN

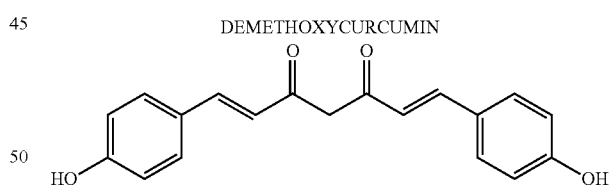

TETRAHYDRO CURCUMIN;

Curcumin (LXXXII)
Demethoxycurcumin (LXXXIII)
Bisdemethoxycurcumin (LXXXIV)
Tetrahydrocurcumin (LXXV)

Verbena (*Verbena officinalis*):

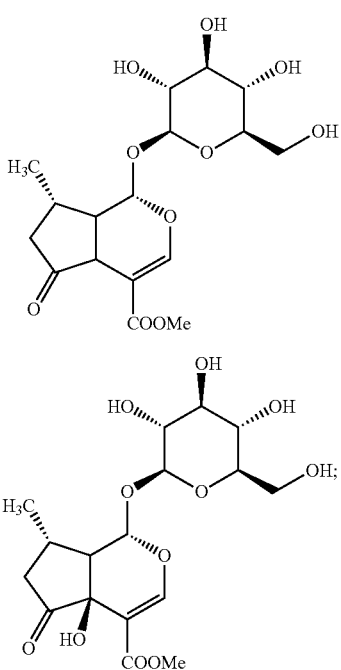

Verbenalin (LXXXVI)

Hastatoside (LXXXVII), and

Yellow Dock (*Rumex crispus*):

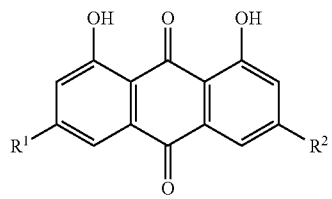

$R^1$ = H, $R^2$ = $CH_3$ (LXXXVIII)
$R^1$ = H, $R^2$ = $CH_2OH$ (LXXXIX)
$R^1$ = OH, $R^2$ = $CH_3$ (XC);

Chrysophenol (LXXXVIII)

Aloe-Emodin (LXXXIX)

Emodin (XC).

The reaction of a keto-hydroxy acid or its derivative, such as ascorbic acid (XLVI) or ascorbyl palmitate (XCI), with an antioxidant anti-inflammatory ketone can proceed in two manners. In case of ascorbic acid, for example, there are two vicinal hydroxy groups that can each react with said ketone to form (XCII), (XCIII), and/or (XCIV), depending on reaction stoichiometry and conditions. When one of the hydroxy groups of said two vicinal hydroxy groups is protected, such as in ascorbyl palmitate, only the unprotected vicinal hydroxy groups react with said ketone to form the corresponding (XCV). It is worthy of note that (XCIII) is the only compound that can form an acid-base salt with a metal or an amine. When the product is a metal complex, the metal is selected from Li, Na, K, Ti, V, Cr, Mn, Fe, Co, Ni, Cu, Zn and Se:

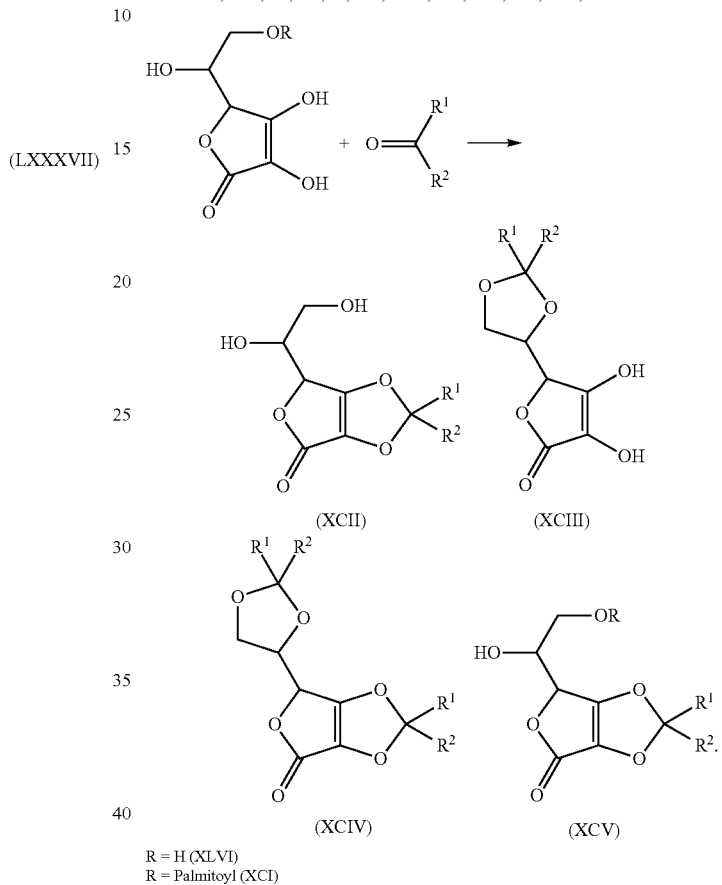

R = H (XLVI)
R = Palmitoyl (XCI)

The reaction of ascorbic acid (XLIV) with phloridzin (LII), an antioxidant ketone from apple skin, provides ascorbyl complex, 2-(3,5-dihydroxy-2-[3-(4-hydroxyphenyl)propanoyl]phenyl beta-D-glucopyranosyl)-2-methyl-furo[3,4-d][1,3]dioxol-4-[6H]-one of formula (XCVI) and its isomer, 2-(2,4-dihydroxy-6-(2S,3R,4R,5S)-2-(hydroxymethyl)-6-methoxytetrahydro-2H-pyran-3,4,5-triolyl)phenyl)-2-ethyl-6-hydroxy-6-(hydroxymethyl)furo[3,4-d][1,3]dioxol-4 (6H)-one of formula (XCVII);

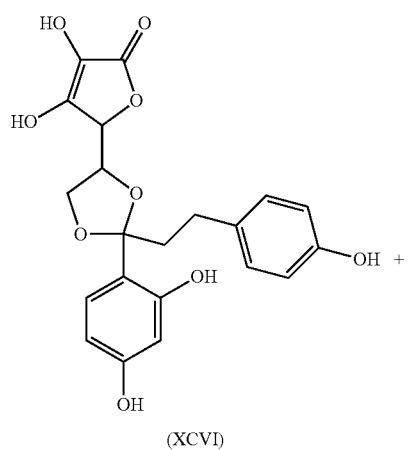
(XCVI)
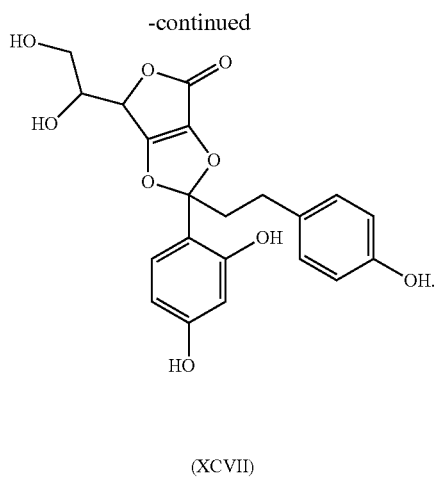
(XCVII)
The reaction of ascorbic acid (XLIV) with phloretin (LIII), another antioxidant ketone from apple skin, provides the complex, 2-(3-(4-hydroxyphenyl)-1-(2,4,6-trihydroxyphenyl)propanyl)-2-methyl-furo[3,4-d][1,3]dioxol-4-[6H]-one (XCVIII) and its isomer, (XCIX);
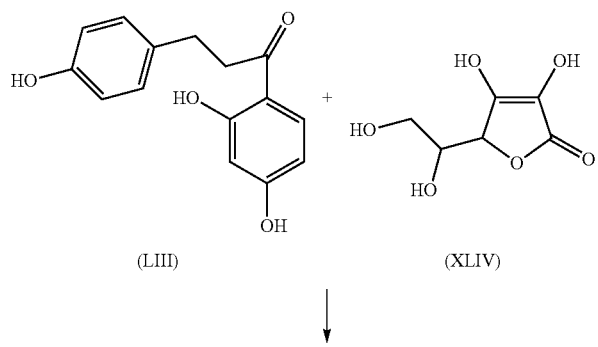
(LIII)      (XLIV)
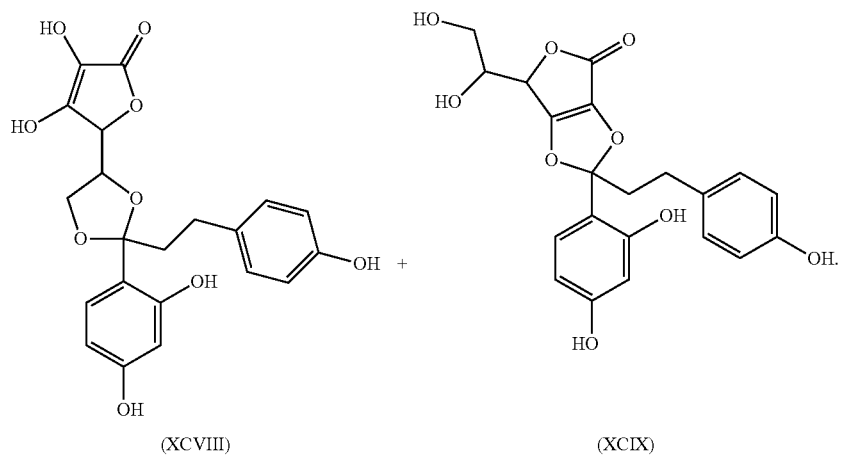
(XCVIII)      (XCIX)

The reaction of mangiferin (LXXI) and ascorbic acid (XLIV) provides (C) and isomer, (CI):

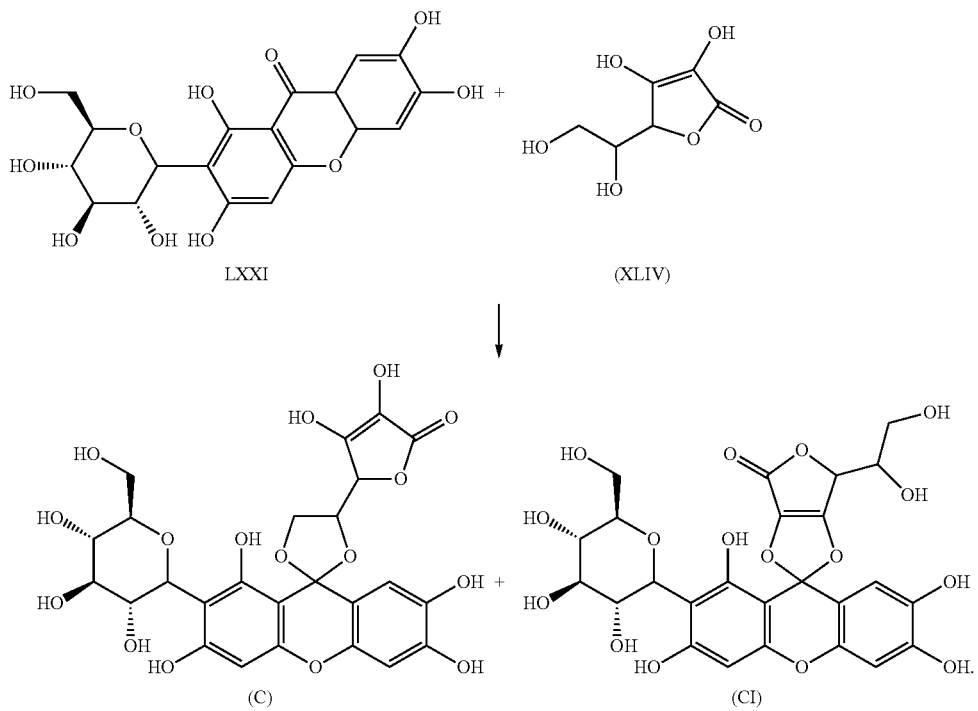

Aloesin is well known for its antioxidant, skin whitening, and anti-inflammatory properties in the prior art: Aloesin up-regulates cyclin kinase activity via inducing the protein levels of cyclin E: K. Y. Lee, et al.; Biochem. Mol. Biol. Int. 41, 285 (1997); Aloesin inhibits hyperpigmentation induced by UV radiation: S. Choi, et al.; Clin. Exp. Dermatol. 27, 513 (2002); Antioxidant, free radical scavenging and anti-inflammatory effects of aloesin derivatives in Aloe vera: A. Yagi, et al.; Planta Med. 68, 957 (2002); Modulation of melanogenesis by aloesin: a competitive inhibitor of tyrosinase: K. Jones, et al.; Pigment Cell Res. 15, 335 (2002); Mushroom tyrosinase inhibition activity of some chromones: L. Z. Piao, et al.; Chem. Pharm. Bull. (Tokyo) 50, 309 (2002); Aloesin and arbutin inhibit tyrosinase activity in a synergistic manner via a different different action mechanism, Ying Hua Jin, Suk Jin Lee, Myung Hee Chung, Jeong Hill Park, Young In Park, Tae Hyeong Cho and Seung Ki Lee, Archives of Pharmacal Research, Volume 22, Number 3, 232-236 (1999), and Aloeresin I, an anti-inflammatory 5-methylchromone from cape aloe: G. Speranza, et al.; Planta Med. 71, 79 (2005).

The ascorbyl complexes of aloesin, (XLVIII) and (XLIX), provide synergistically combined and bioavailability-enhanced cellular benefits of individual reactant components, aloesin and ascorbic acid.

It is both surprising and unexpected that, under certain conditions, "complexes" of the present invention can undergo an isomerization to 8,9-Dihydroxy-1,3,6-trioxaspiro[4.4]non-8-en-7-ones, or vice versa, as illustrated in FIG. 2.

[FIG. 2]. Isomerization of Furo[3,4-d]dioxol-4[6H]one.

Additional examples of ketones suitable in the process of the present invention include, but not limited to acetophenone, 2-hydroxyacetophenone, 3-hydroxyacetophenone, 4-hydroxyacetophenone, 2,3-dihydroxyacetophenone, 2,4-dihydroxyacetophenone (resacetophenone, acetyl resorcinol)), 2,5-dihydroxyacetophenone (2-acetyl quinol; quinacetophenone), 2,6-dihydroxyacetophenone, 3,4-dihydroxyacetophenone, 3,5-dihydroxyacetophenone, 2,4,6-trihydroxyacetophenone (phloracetophenone), 2,3,4-trihydroxyacetophenone, 2,3,5-trihydroxyacetophenone, 2,3,6-trihydroxyacetophenone, 2,4,5-trihydroxyacetophenone, 3,4,5-trihydroxyacetophenone, Resacetophenone, 2-Acetyl resorcinol, 4-Acetyl resorcinol, 3,4-Dihydroxyacetophenone, acetyl quinol, Phloridzin, Phloretin, Quinacetophenone, 1-(3-Hydroxy-4-methoxy-5-methylphenyl)ethanone, 1-(3-hydroxy-4-methoxyphenyl)ethanone, Paeonol, 2-hydroxypropiophenone, 3-hydroxypropiophenone, 4-hydroxypropiophenone, 2,3-dihydroxypropiophenone, 2,4-dihydroxypropiophenone, 2,5-dihydroxypropiophenone, 2,6-dihydroxypropiophenone, 3,4-dihydroxypropiophenone, 3,5-dihydroxypropiophenone, 2,4,6-trihydroxypropiophenone, 2,3,4-trihydroxypropiophenone, 2,3,5-trihydroxypropiophenone, 2,3,6-trihydroxypropiophenone, 2,4,5-trihydroxypropiophenone, 3,4,5-trihydroxypropiophenone, and combinations thereof. Also, the plant extracts that contain hydroxy ketones, for example, peony extract, Primula extract, and Apple root extract, can also be used in this process.

The examples of hydroxy propiophenone compounds used in the process of the present invention include 2-hydroxypropiophenone, 3-hydroxypropiophenone, 4-hydroxypropiophenone, 2,3-dihydroxypropiophenone, 2,4-dihydroxypropiophenone, 2,5-dihydroxypropiophenone, 2,6-dihydroxypropiophenone, 3,4-dihydroxypropiophenone, 3,5-dihydroxypropiophenone, 2,4,6-trihydroxypropiophenone, 2,3,4-trihydroxypropiophenone, 2,3,5-trihydroxypropiophenone, 2,3,6-trihydroxypropiophenone, 2,4,5-trihydroxypropiophenone, 3,4,5-trihydroxypropiophenone, 1-(2,4-dihydroxyphenyl)-2-hydroxyethanone, (2-hydroxyphenyl)(oxo)acetic acid, 1-(2,6-dihydroxyphenyl)-1-butanone, 1-(1-hydroxy-2-naphthyl)ethanone, 1-(2-hydroxy-1-naphthyl)ethanone, 5,7-dihydroxy-1-indanone, 1-(2-hydroxy-5-methylphenyl)-1,3-butanedione, N-(4-acetyl-3-hydroxyphenyl)acetamide, 4-acetyl-3-hydroxyphenyl acetate, 1,1'-(4,6-Dihydroxy-1,3-phenylene)bisethanone, 1-(1-hydroxy-2-naphthyl)ethanone, 2,3-Dihydro-9,10-dihydroxy-1,4-anthracenedione, and combinations thereof.

The ketones of the present invention can have additional cyclic rings attached at the aromatic moiety. Such attached rings can be alicyclic, aromatic, heterocyclic, or a combination thereof, examples of which include 1-hydroxy-2-acetylnaphthalene; 1-hydroxy-2-acetyl-5,6,7,8-tetrahydro-naphthalene; 7-acetyl-8-hydroxyquinoline; 3-acetyl-4-hydroxyacridine; 6-acetyl-7-hydroxybenzothiazole.

It has additionally been found that the ketone or substituted ketone moiety can also be attached to a nitrogen heteroaromatic ring at a position adjacent to the ring nitrogen atom, for example, additional nitrogen atoms, or sulfur or oxygen atoms, or a combination thereof. The examples of hetero-aromatic ring structures include 2-acetylpyridine, 2-acetylpyrrole, 2-acetylimidazole, 2-acetylthiazole, 2-acetylpyrimidine, 2-acetylindole, 2-acetyl-1-methylpyrrole, 2-acetyl-4-methylpyridine, 1-acetylphenothiazine, 2-hydroxy-1-acetylphenothiazine, 8-hydroxy-9-acetylphenanthrene, 2-acetylpyrazine, 2-acetylquinoline, 2-acetyl-8-hydroxyquinoline, 2-acetyltryptophane, 2-acetyltryptophanamide, 2-acetylpyridine N-oxide, 2-acetylquinazoline, 2-acetylquinoxaline, 3-acetylpyridazine, 6,6'-diacetyl-2,2'-pyridyl, 3-actyl-1,2,4-trizol, and their other acetyl side chain substituted and/or hetero-aromatic ring substituted derivatives.

Additional heteroatom substituents in the nitrogen heteroatom ring with an alkyl ketone moiety or their derivatives are also included; for example, in case of five- and six-member nitrogen heteroatom rings in which two additional nitrogen heteroatoms are included, a large variation in five- and six-member multi-heteroatom ring structures is possible.

In the process of the preparation of "complexes" of the present invention said ascorbic acid derivatives are selected from various alkyl and aryl esters of ascorbic acid, ethers of ascorbic acid, inorganic esters of ascorbic acid, and acetals and ketals of ascorbic acid. Non-exclusive examples of the ascorbic acid derivatives are, for instance, the alkyl esters of L-ascorbic acid where the alkyl portion has from 1 to 20 carbon atoms. With respect to the esters, they may be selected from the group consisting of fatty acid mono-, di-, tri- or tetra-esters of ascorbic acid. For example, such esters include, but are not limited to ascorbyl acetate, ascorbyl palmitate, ascorbyl laureate, ascorbyl myristate, ascorbyl stearate, ascorbyl dipalmitate, ascorbyl dilaurate, ascorbyl dimyristate, ascorbyl distearate, ascorbyl tripalmitate, ascorbyl trilaurate, ascorbyl trimyristate, ascorbyl tristearate, ascorbyl tetrapalmitate (tetrahexyldecyl ascorbate), ascorbyl tetralaurate, ascorbyl tetramyristate, ascorbyl tetrastearateL-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate, tetrahexyl decyl ascorbate; phosphates of L-ascorbic acid such as L-ascorbyl-2-phosphate and L-ascorbyl-3-phosphate; sulfates of L-ascorbic acid such as L-ascorbyl-2-sulfate and L-ascorbyl-3-sulfate; their salts with alkaline earth metals such as calcium and magnesium.

In the process of the preparation of Furo[3,4-d][1,3]dioxol-4(6H)-ones of the present invention said solvent or reaction medium is selected from water, ethanol, glycerin, ethylene glycol, propylene glycol, butylene glycol, hexylene glycol, pyrrolidone, N-methylpyrrolidone, dimethyl sulfoxide, dimethyl sulfone, polyethylene glycol, polypropylene glycol, methylpropanediol, Triethyl citrate, and such, and combinations thereof.

Also, this process can be performed in a single step via a novel in-situ method. In the preparation of a skin lotion or cream composition, for example, all other ingredients of said composition can be mixed and processed and said ketone and said ascorbic acid or its derivative can then be added to the composition, wherein the corresponding Furo[3,4-d][1,3]dioxol-4(6H)-one is thus formed in-situ. Alternatively, ketone can first be reacted with ascorbic acid or its derivative in the presence of a solvent as a processing aid, and resulting Furo[3,4-d][1,3]dioxol-4(6H)-one can then be utilized in any subsequent preparation.

The ketones used in the present invention can be from various sources, such as from chemical synthesis or from natural origin such as plants, various plant parts (leaf, root, flower, bark, seed, et cetera). Hydroxy ketones are well known from the plant sources; for example, acetophenone derivatives such as Paeonol (3-hydroxy-5-methoxy acetophenone), 2,5-Dihydroxy-4-Methoxy Acetophenone, and 2,5-Dihydroxy-4-Methyl Acetophenone, have been obtained from Chinese peony. Quinacetophenone (2-acetyl hydroquinone) has been obtained from primrose (*Primula Ovalifolia*). Scutellarin and Scutellarein (hydroxy benzopyranones) have been obtained from *Scutellaria* plants. Xanthoxyline (2-hydroxy-4,6-dimethoxyacetophenone) has been isolated from *Sebastiania schottiana*. Acetophenone derivatives, such as 1-(3-Hydroxy-4-methoxy-5-methylphenyl)ethanone and 1-(3-hydroxy-4-methoxyphenyl)ethanone have been identified from stem bark of *Lamprothamnus zanguebaricus*. Apocynin (4-hydroxy-3-methoxyacetophenone) is a well-known acetophenone derivative isolated from the traditional medicinal plant *Picrorhiza kurroa*. 4-Hydroxyacetophenone has been obtained from *Ligularia vellerea*. These acetophenone derivatives are known for their antioxidant, microcirculation improvement, anti-inflammatory, MAO inhibition, and histamine suppression benefits. *Primula obconica* was introduced to Europe from Hubei, China in 1880, and has been cultivated worldwide as one of popular ornamental plants. *Primula obconica* extract has been shown to contain acetyl hydroquinone and methyl acetyl hydroquinone [Nan et al., Z. Naturforsch., 58, 57-61 (2003)]. Peony root bark (*Paeonia Suffruticosa* Radix) contains high levels of Paeonol (2-Hydroxy-4-methoxy acetophenone). Apple root contains Phloridzin and Phloretin. The extracts, both in crude form or in highly refined form, are suitable for applications of the present invention.

It is preferred to have the pH of the reaction medium on the acidic side, from a pH of about 2.0 to about 5.5. For this reason, an acidulant or acid releasing agent, such as a lactone, can be included. An organic hydroxy acid or hydroxy lactone is preferred, the examples of which include but not limited to glycolic acid, benzilic acid, tropic acid, lactic acid, malic acid, citric acid, isocitric acid, citramalic acid, tartronic acid, tartaric acid, gluconic acid, galactonic acid, alpha-hydroxy-iso butylic acid, phenyl-lactic acid, muldic acid, atrolactic acid, gluconolactone, galactonolactone, ribonic acid, ribonolactone, pantoic acid, pantolactone, pantotheinic acid, alpha-hydroxybutylic acid, beta-hydroxybutylic acid, quinic acid, pyruvic acid, phenylpyruvic acid, Mandelic acid, Salicylic acid, tetronic acid, phytic acid, and ascorbic acid. When utilizing ascorbic acid itself, an excess of ascorbic acid is preferred to assure desired pH conditions. Relative to the use of lactones, hydroxy lactones are most preferred, which include gluconolactone, erythronolactone, Isocitric acid lactone, glucooctanolactone, galactonolactone, gulonolactone, sugar lactone, mannonolactone, saccharolactone, glucoronolactone, and ribolactone, and their corresponding acid forms. The acid form of gluconolactone, for example, is gluconic acid. Mineral acids, such as sulfuric acid, oleum, and phosphoric acid, which have been used extensively in the prior art for the preparation of acetals and ketals of ascorbic acid, are not preferred in the preparation of Furo[3,4-d][1,3]dioxol-4(6H)-ones of the present invention. However, acid-form of certain sulfonated ion exchange resins can be used in the process of the present invention.

The present invention also discloses a method for topical application of said "complexes" for the treatment of skin condition. The method of treatment for skin condition comprises of (i) the topical application of a composition consisting of a compound on an afflicted area, and, wherein, (ii) Said application is repeated to complete the treatment as desired, and (iii) This method can include a base or carrier.

In a surprising and unexpected discovery, "complexes" of the present invention are useful for treatment of certain topical conditions, including the modulation of certain enzymes such as Phenylalanine Hydroxylase, Tyrosine Transaminase, Phenylalanine Transaminase, Tyrosinase, various MMP (Matrix metalloproteases), and Superoxide dismutase.

It is postulated that "complexes" of the present invention, when absorbed into skin and after having reached the physiological pH of approximately 7.4 undergo a thermodynamically-controlled chemical reversal and regenerate the original chemical agents [FIG. 1]. It is postulated that this may be due to greater thermodynamic stability provided by ascorbate anion at said pH.

[FIG. 1]. Reversion of a Furo[3,4-d]dioxol-4[6H]one into Ascorbic Acid and Ketone.

Inhibition of Matrix Metalloproteases (MMP).

Matrix metalloproteases (MMP) are naturally occurring enzymes found in most mammals and are zinc-dependent endopeptidases that perform extracellular tissue reorganization (matrix reorganization). One major biological function of the matrix metalloprotease (MMP) is to catalyze the breakdown of connective tissue or extracellular matrix by virtue of their ability to hydrolyze various components of the tissue or matrix. Examples of the components that may be hydrolyzed by an MMP include collagens (for example, Collagenases type I, II, III, or IV), gelatins (for example, Gelatinases), proteoglycans, and fibronectins. Apart from their role in degrading connective tissue, MMPs are also involved in the activation of the zymogen (pro) forms of other MMPs thereby inducing MMP activation (proenzyme activation). They are also involved in the biosynthesis of TNF-alpha which is implicated in many pathological conditions and can cause or contribute to the effects of inflammation, rheumatoid arthritis, asthma, COPD, autoimmune disease, multiple sclerosis, graft rejection, fibrotic disease, cancer, infectious diseases, malaria, mycobacterial infection, meningitis, fever, psoriasis, cardiovascular/pulmonary effects (e.g., post-ischemic reperfusion injury), congestive heart failure, hemorrhage, coagulation, hyperoxic alveolar injury, radiation damage, cachexia, anorexia, and acute phase responses like those seen with infections and sepsis and during shock (e.g., septic shock and hemodynamic shock).

Over 30 MMPs have been characterized so far in humans and several major groups have been determined based on substrate specificity, some of which are described below, and are believed applicable to the present invention.

MMP-1 (also known as collagenase 1, or fibroblast collagenase). The substrates of MMP-1 include collagen I, II, and III; gelatin, and proteoglycans. Over-expression of this enzyme is believed to be associated with emphysema, with hyperkeratosis and atherosclerosis, over-expressed alone in papillary carcinoma.

MMP-2 (also known as gelatinase A, basement membrane collagenase, or proteoglycanase). The substrates of MMP-2 include collagen I, collagen II, collagen IV, collagen V, collagen VII, collagen X, collagen XI, collagen XIV, elastin, fibronectin, gelatin, nidogen, believed to be associated with tumor progression through specificity for type IV collagen (high expression observed in solid tumors and believed to be associated with their ability to grow, invade, develop new blood vessels and metastasize) and to be involved in acute lung inflammation and in respiratory distress syndrome.

MMP-3 (also known as stromelysin 1). The substrates of MMP-3 include collagen III, collagen IV, collagen V, collagen IX, collagen X, laminin, nidogen, overexpression believed to be involved in atherosclerosis, aneurysm and restenosis.

MMP-7 (also known as matrilysin). The substrates of MMP-7 include collagen IV, elastin, fibronectin, gelatin, laminin.

MMP-8 (also known as collagenase 2, or neutrophil collagenase). The substrates of MMP-8 include collagen I, collagen II, collagen III, collagen V, collagen VII, collagen IX, gelatin over-expression of which can lead to non-healing chronic ulcers.

MMP-9 (also known as gelatinase B, or 92 kDa gelatinase). The substrates of MMP-9 include collagen I, collagen III, collagen IV, collagen V, collagen VII, collagen X, collagen XIV, elastin, fibronectin, gelatin, nidogen The above enzyme is believed to be associated with tumor progression through specificity for type IV collagen, to be released by eosinophils in response to exogenous factors such as air pollutants, allergens and viruses, to be involved in the inflammatory response in asthma and to be involved in acute lung inflammation and respiratory distress syndrome. The applicants believe that an inhibitor for this enzyme would be effective in the treatment of chronic obstructive pulmonary disorder (COPD) and/or asthma.

MMP-10 (also known as stromelysin 2). The substrates of MMP-10 include collagen III, collagen IV, collagen V, elastin, fibronectin, and gelatin.

MMP-11 (also known as stromelysin 3). The substrates of MMP-11 include serine protease inhibitors (Serpins).

MMP-12 (also known as metalloelastase, human macrophage elastase, or HME). The substrates of MMP-12 include fibronectin, laminin, believed to play a role in tumor growth inhibition and regulation of inflammation and to play a pathological role in emphysema and in atherosclerosis, aneurysm and restenosis. The applicants believe that an inhibitor for this enzyme would be effective in the treatment of chronic obstructive pulmonary disorder (COPD) and/or asthma.

MMP-13 (also known as collagenase 3). The substrates of MMP-13 include collagen I, collagen II, collagen III, collagen IV, collagen IX, collagen X, collagen XIV, fibronectin, and gelatin, recently identified as being over-expressed alone in breast carcinoma. The applicants believe that an inhibitor for this enzyme would be effective in the treatment of breast cancer and arthritis.

MMP-14 (also known as membrane MMP or MT1-MMP). The substrates of MMP-14 include MMP-2, collagen I, collagen II, collagen III, fibronectin, gelatin, laminin.

MMP-15 (also known as MT2-MMP). The substrates of MMP-15 include MMP-2, collagen I, collagen II, collagen III, fibronectin, laminin nidogen.

MMP-16 (also known as MT3-MMP). The substrates of MMP-16 include MMP-2, collagen I, collagen III, and fibronectin.

MMP-17 (also known as MT4-MMP), substrates fibrin (fibrinogen).

MMP-18 (also known as collagenase 4).

MMP-19 (also known as Rasi-1). The substrates of MMP-19 include MMP-9, gelatin, laminin-1, collagen IV, and fibronectin.

MMP-20 (also known as enamelysin), substrate amelogenin.

MMP-23 (also known as femalysin), substrate gelatin.

MMP-24 (also known as MT5-MMP). The substrates of MMP-24 include MMP-2, gelatin, fibronectin, chondroitin, and dermitin sulfate proteoglycans.

MMP-25 (also known as MT6-MMP). The substrates of MMP-25 include MMP-2, gelatin, collagen IV, and fibronectin.

MMP-26 (also known as matrilysin 2 or endometase). The substrates of MMP-26 include denatured collagen, fibrinogen, fibronectin, vitronectin.

MMP-28; also known as epilysin, substrates caesin.

Over-activation of a matrix metalloprotease ("MMP"), or an imbalance between an MMP and a natural (i.e., endogenous) tissue inhibitor of a matrix metalloprotease ("TIMP"), has been linked to the pathogenesis of diseases characterized by the breakdown of connective tissue or extracellular matrix. Examples of diseases characterized by over-expression and/or over-activation of an MMP include rheumatoid arthritis, asthma, COPD, osteoarthritis; osteoporosis; periodontitis; multiple sclerosis; gingivitis; corneal, epidermal, and gastric ulceration; atherosclerosis; neointimal proliferation, which leads to restenosis and ischemic heart failure; stroke; renal disease; macular degeneration; and tumor metastasis.

Further, some MMP-mediated diseases may involve over activity of only one MMP enzyme. This is supported by the recent discovery that MMP-13 alone is over-expressed in breast carcinoma, while MMP-1 alone is over-expressed in papillary carcinoma.

Research has been carried out into the identification of inhibitors that are selective, for example, for a few of the MMP subtypes. A MMP inhibitor of improved selectivity would avoid potential side effects associated with inhibition of MMPs that are not involved in the pathogenesis of the disease being treated. Further, use of more selective MMP inhibitors would require administration of a lower amount of the inhibitor for treatment of disease than would otherwise be required and, after administration, partitioned in vivo among multiple MMPs. Still further, the administration of a lower amount of compound would improve the margin of safety between the dose of the inhibitor required for therapeutic activity and the dose of the inhibitor at which toxicity is observed. Gupta (U.S. patent application Ser. No. 20060074108) discusses some of these approaches and provides prior art citations.

The "complexes" and compositions comprising the "complexes" of the present invention, surprisingly and unexpectedly inhibit MMP, thus providing excellent anti-inflammatory benefits, especially when administered via topical method of the present invention.

Skin Brightening and Antiwrinkle—Antiaging Applications.

The "complexes" of the present invention provide an unexpected reduction of melanin, especially when administered via topical method of the present invention. The mechanism of this action is not clear at this stage. However, it is speculated that the ascorbate portion of the "complexes" of the present invention reduces melanin color by chemical reduction of color forming conjugated double bonds of melanin. Additionally, ketone part of the "complexes" of the present invention causes the inhibition of tyrosinase via its anti-inflammatory and MMP inhibitory action. This unprecedented dual mechanism results in a superior brightening of dark skin, reduction of age spots, and prevention of skin darkening upon exposure to sun and UV.

Collagen Synthesis Enhancement.

The "complexes" of the present invention provide a surprising and unexpected enhancement of collagen in skin. This results in increased suppleness and pliability of skin and wrinkles reduction.

The "complexes" of the present invention can be formulated in various cosmetic and pharmaceutical consumer product compositions, delivery systems, and carrier bases utilizing a variety of delivery systems and carrier bases. Such consumer products include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system or a carrier base are selected in the form of a lotion, cream, gel, spray, thin liquid, body splash, powder, compressed powder, tooth paste, tooth powder, mouth spray, paste dentifrice, clear gel dentifrice, mask, serum, solid cosmetic stick, lip balm, shampoo, liquid soap, bar soap, bath oil, paste, salve, collodion, impregnated patch, impregnated strip, skin surface implant, impregnated or coated diaper, and similar delivery or packaging form.

In another preferred aspect, the delivery system can be traditional water and oil emulsions, suspensions, colloids, microemulsions, clear solutions, suspensions of nanoparticles, emulsions of nanoparticles, or anhydrous compositions.

Antioxidant Application.

The "complexes" of the present invention provide surprisingly unexpected intracellular and extracellular antioxidant properties. It is usually either an extracellular or an intracellular antioxidant benefit that is provided by any single agent. Thus, the "complexes" of the present invention offer novel multi-function benefits. This is of great commercial and consumer significance with current trend of worldwide aging population.

With an aging population, there has been an increase in the study of aging as it relates to the human body and, more particularly, human skin. For example, the treatment of aging skin exhibited by the presence of fine lines, wrinkles, and the like has received a great deal of attention. The dermal signs of aging such as fine lines, wrinkles, laxity, and hyperpigmentation have been fought through many tactics including surgery, laser treatment and cosmetics. Cosmetic treatments include the use of various creams and lotions to alter the effects of dermal aging. Much of the literature in the prior art focuses on the use of a single primary component to prevent one of several deleterious aging affects. For example, one tactic has been to use one or more hydroxy acids or retinoic acid to stimulate the re-growth of dermal cells, without other components. This approach is flawed because it does not recognize that aging is caused by the deleterious interaction of multiple agents on the skin, from multiple sources, causing damage to the skin through multiple simultaneous damage pathways.

More comprehensive studies have found that environmental factors, such as stress, sun exposure, and impurities in food, water, and air, also adversely effect components of the epidermal and dermal layers of the skin which, in turn, impact and alter the appearance of the skin and lead to an appearance of premature aging. For example, factors such as free radicals, reactive nitrogen species ("RNS"), reactive oxygen species ("ROS"), and other oxidizing species ("OOS") that may or may not possess characteristics of each free radicals, RNS, and ROS, can adversely impact the human body including the skin. Particular factors within the groups noted above that have been found to impact and adversely affect the appearance of the skin include nitric oxide, superoxide radicals, hydrogen peroxide, and hydroxide free radicals. These factors have been variously implicated in a number of skin conditions including photo damage, general aging of the skin, contact dermatitis, wrinkling, lipid peroxidation, enzyme degradation, reduction and breakdown of collagen and/or elastin, degradation and inhibited reproduction of DNA, inflammation, and general damage to the skin tissue.

The ROS species include superoxide (O2-), hydrogen peroxide (H2O2), peroxy radicals (HO2 and RO2) alkyl peroxide (R2O2), hydroxyl radical (OH), alkoxy radical (OR), and singlet oxygen. The OOS species include hypohalous acids (HOX) (where X is chloride, bromide, iodide), Z-amines (where Z is either chlorinated or ammoniated amine containing compounds, the reactive nitrogen species ("RNS") nitric oxide (NO), ammonia, cyclooxygenase, phospholipase A2, phospholipase C and transition metals.

Each of the ROS directly or acting as an intermediate are thought to act on cell membrane and/or other cellular components including organelles and their contents to adversely impact the skin. Thus, there is a need for a topical skin treatment composition and method that provides a defense against each of the ROS, RNS, and OOS noted above. In addition, it would be desirable if such a composition repaired damage caused by the ROS, RNS, and OOS noted above.

The compositions of the present invention are directed to components that provide a defense against the various pathway mechanisms of free radicals, reactive oxygen species, reactive nitrogen species, and other oxidizing species noted above that adversely affect the human body, including the skin. The present inventions, therefore, also include methods for applying the compositions of the invention to the skin, to inhibit the causative factors that adversely affect the skin, and thereby treat and improve the quality of the skin. Generally, the compositions and methods of this invention are directed to the prevention of the adverse or detrimental effects of free radicals, reactive oxygen species, reactive nitrogen species, and other oxidizing species noted above, on the human body, including the skin. Thus, the preset invention includes various compositions that include at least one anti-free radical component and/or an anti-superoxide component and/or an anti-hydrogen peroxide component and/or an anti-hydroxyl radical component and/or a chain-breaking component. Moreover, most, if not all, of the above beneficial functions can be provided by multi-functional Furo[3,4-d][1,3]dioxol-4(6H)-ones of the present invention.

Formulation of "Complexes" in Topical Compositions.

Additional cosmetically or pharmaceutically beneficial ingredients can also be included in the compositions consisting the "complexes" of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable compositions further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylans, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum traganacanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable compositions may include surface-active agents. Surface-active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used in this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecylbenzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL. as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions comprising the "complexes" of the present invention may include long chain fatty amines from about $C_{10}$ to $C_{22}$ and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable compositions comprising the "complexes" of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable compositions comprising the "complexes" of the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH.sub.2).sub.3 radical is attached to the nitrogen atom of the betaine are also useful in this invention.

The anionic, cationic, nonionic, amphoteric or zwitterionic surface-active agents used in the cosmetically acceptable compositions of this invention are typically used in an amount from about 0.1 to 50 percent by weight, preferably from about 0.5 to about 40 percent by weight, more preferably from about 1 to about 20 percent by weight.

The cosmetically acceptable compositions comprising the "complexes" of the present invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable compositions comprising the "complexes" of the present invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition comprising the "complexes" of the present invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, C.sub.12 to C.sub.16 fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention comprising the "complexes" of the present invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions comprising the "complexes" of the present invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane-200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions comprising the "complexes" of the present invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions comprising the "complexes" of the present invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is $C_{12}$ to $C_{14}$ isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions comprising the "complexes" of the present invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable compositions comprising the "complexes" of the present invention may include one or more rheological modifiers. The rheological modifiers that can be used in this invention include high molecular weight crosslinked homopolymers of acrylic acid, and Acrylates/C10-30 Alkyl Acrylate Crosspolymer, such as the Carbopol and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable compositions may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 20 weight percent, preferably 0.5 to 10 weight percent and most preferably from 1.0 to 5.0 weight percent of the cosmetically acceptable composition.

The cosmetically acceptable composition comprising the "complexes" of the present invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl)aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable compositions comprising the "complexes" of the present invention may include one or more preservatives. Example of preservatives, which may be used include, but are not limited to 1,2-dibromo-2,4-dicyano butane (Methyldibromo Glutaronitrile), benzyl alcohol, imidazolidinyl urea, 1,3-bis (hydroxymethyl)-5,5-dimethyl-2,3-imidazolidinedione (e.g., DMDM Hydantoin), methylchloroisothiazolinone and methylisothiazolinone (e.g. Kathon), methyl paraben, propyl paraben, phenoxyethanol, ethylhexylglycerin, chlorphenesin, and sodium benzoate, and mixtures thereof.

The cosmetically acceptable compositions comprising the "complexes" of the present invention may comprise peptides, the examples of which include Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, and Acetyl Tetrapetide-2.

The cosmetically acceptable compositions comprising the "complexes" of the present invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable compositions comprising the "complexes" of the present invention can be presented in various forms. Examples of such forms include, but are not limited a solution, liquid, cream, emulsion, dispersion, gel, and thickening lotion.

The cosmetically acceptable compositions comprising the "complexes" of the present invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture from 0.1 to 70 percent by weight, relative to the weight of the total composition.

The cosmetically acceptable composition comprising the "complexes" of the present invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable compositions comprising the "complexes" of the present invention can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions comprising the "complexes" of the present invention for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions comprising the "complexes" of the present invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions comprising the "complexes" of the present invention for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions comprising the "complexes" of the present invention are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetic compositions comprising the "complexes" of the present invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The cosmetically acceptable carrier comprising the "complexes" of the present invention may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonite, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion comprising the "complexes" of the present invention may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension comprising the "complexes" of the present invention may comprise liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar and tragacanth or mixtures of these ingredients.

The formulation of cleansing compositions comprising the "complexes" of the present invention with surfactant may comprise aliphatic alcohol sulfate, aliphatic alcohol ether sulfate, sulfosucinnate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions comprising the "complexes" of the present invention can be included, and selected from but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Clea europaea*), α-Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), Boswellia Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalis sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

The anti-inflammatory ingredients or compositions can be selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andrographolide, Grapeseed extract, Green Tea Extract, Polyphenols, Pycnogenol (Pine Bark extract), White Tea extract, Black Tea extract, (*Andrographis paniculata*), Carnosine, Niacinamide, and *Emblica* extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), *Emblica* extract (*Phyllanthus emblica* extract), Asiaticoside (*Centella asiatica* extract), Boswellia Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis-Vinifera*) leaves, apigenin, phytosan, luteolin, and combinations thereof.

Certain divalent and polyvalent metal ions can also be present in the compositions of the present invention. The examples of such metal ions include zinc, copper, manganese, vanadium, chromium, cobalt, and iron.

EXAMPLES

All Quantities are in Weight Percent Amounts

The examples do not limit the scope of the present invention.

Example 1

Preparation of Ascorbyl Complex of Formula (I), Substituent (XLI), R=H from Ascorbic Acid and Resacetophenone

Ingredients. (1) Water 5.0 (2) Ascorbic Acid 5.0 (3) Resacetophenone 2.0 (4) Butylene Glycol 88.0. Procedure. Ingredients 1 and 2 are mixed and heated at 60 to 65 C till a solution is obtained. Ingredients 3 and 4 are mixed and heated at 60 to 65 C till a solution is obtained. The two solutions are mixed and heated at 80 to 85 C for 30 to 45 minutes, then cooled to room temperature. A solution of said ascorbyl complex in butylene glycol—water is thus obtained. For clarity, the structure of said ascorbyl complex is:

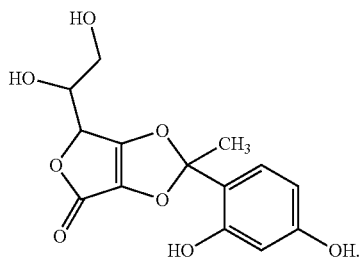

Example 2

Preparation of Ascorbyl Complex of Formula (I), $R^1$=(II), R=H, from Ascorbic Acid and Aloesin

Ingredients. (1) Water 5.0 (2) Ascorbic Acid 4.0 (3) Aloesin 8.0 (4) Butylene Glycol 83.0. Procedure. Ingredients 1 and 2 are mixed and heated at 60 to 65 C till a solution is obtained. Ingredients 3 and 4 are mixed and heated at 60 to 65 C till a solution is obtained. The two solutions are mixed and heated at 80 to 85 C for 30 to 45 minutes, then cooled to room temperature. A solution of said ascorbyl complex in butylene glycol—water is thus obtained. For clarity, the structure of said ascorbyl

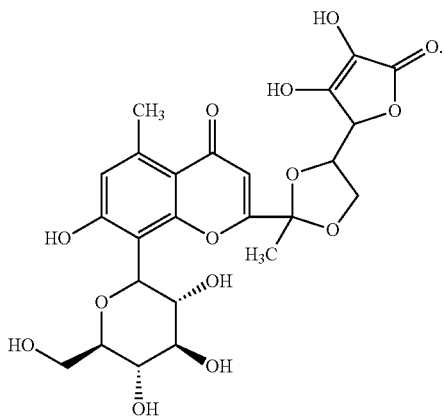

Example 3

Skin Whitening and Anti-Wrinkle Serum Containing In-Situ Generated Ascorbyl Complex of Formula (I), R1=(V), R=H, from Ascorbic Acid and Phloretin

Ingredients. (1) Water 5.0 (2) Ascorbic Acid 3.5 (3) Phloretin 5.5 (4) Butylene Glycol 60.0 (5) Diglycerol 20.0 (6) Dow Corning Cosmetic Wax 2501 4.0 (7) Structure Plus 2.0. Procedure. Ingredients 1 and 2 are mixed and heated at 80 to 85 C till a solution is obtained. Ingredients 3 to 6 are mixed and heated at 60 to 65 C till a solution is obtained. The two solutions are mixed and heated at 60 to 65 C for 30 to 45 minutes, then cooled to 35 to 40 C and ingredient 7 is added with mixing to a desired viscosity. It is cooled to room temperature. A serum-like product is obtained. It contains ascorbyl complex of the following formula:

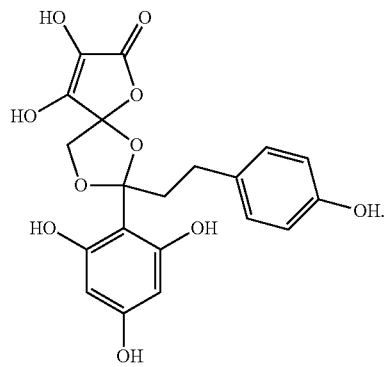

Example 4

Skin Discoloration and Age Spots Serum Containing In-Situ Generated Ascorbyl Complex of Formula (I), $R^1$=(II), R=Palmitoyl from Ascorbyl Palmitate and Aloesin

Ingredients. (1) Ascorbyl Palmitate 5.0 (2) Aloesin 5.0 (3) Butylene Glycol 65.0 (4) Diglycerol 20.0 (5) Dow Corning Cosmetic Wax 2501 5.0. Procedure. Ingredients 1 to 5 are mixed and heated at 80 to 85 C for 2 hours. It is then cooled to room temperature. A serum-like product is obtained. It contains ascorbyl complex of the following formula:

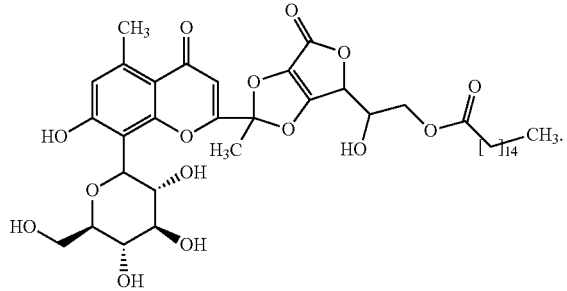

Example 5

Ascorbyl Complex of Formula (I), Substituent (II), R=Palmitoyl from Ascorbyl Palmitate and Aloesin Ingredients. (1) Aloesin 4.00 (2) Ascorbyl Palmitate 4.14 (3) Ethoxydiglycol 91.86. Procedure. Ingredients 1 to 5 are mixed and heated at 80 to 85 C for 2 hours. It is then cooled to room temperature. A serum-like product is obtained. It contains ascorbyl complex of the following formula:

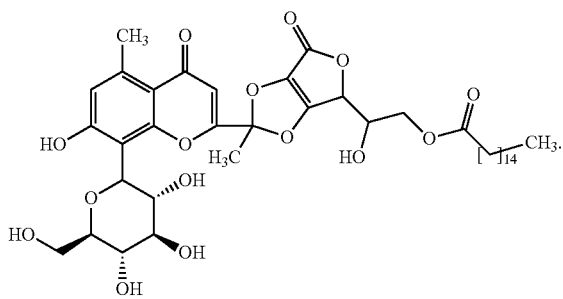

Example 6

Skin Whitening Cream

Ingredients. (1) Water 55.0 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) Boswellia Serrata 0.5 (10) Cetyl Dimethicone 1.5 (11) Tetrahydrocurcuminoids 0.5 (12) Shea butter 2.0 (13) Ximenia oil 1.0 (14) Triethyl citrate 5.0 (15) 6-(1,2-dihydroxyethyl)-2-(2,4-dihydroxyphenyl)-2-methyl-furo[3,4-d][1,3]dioxol-4-[6H]-one 6.0 (16) Paeonol 1.5 (17) Carnosine 0.1 (18) Cyclomethicone, Dimethicone Crosspolymer 2.0 (19) Polysorbate-20 2.0 (20) Ethyl Lactate 12.0. Procedure. Mix (1) to (13) and heat at 70 to 80 C till homogenous. Cool to 40 to 50 C. Premix (14) to (20) and add to batch with mixing. Cool to room temperature. An off-white cream is obtained.

Example 7

MMP Inhibiting Skin Brightening Eye Serum

Ingredients. (1) Butylene Glycol 23.8 (2) Methylpropanediol 25.8 (3) Hydroxypropyl Cellulose 0.25 (4) Mango butter 2.0 (5) Gluconolactone (5.0) (6) Ascorbic acid 10.0 (7) 2-Hydroxy Acetophenone 1.5 (8) Methylpropanediol 30.35 (9) Preservative 0.8. (10) Titanium Dioxide 0.5. Procedure. Mix (1) to (3) and heat at 85 to 95 C till a clear solution is obtained. Premix all other ingredients and heat to 45 to 50 C. Add premix to main batch and mix, and then cool to room temperature. A white, lotion-like serum is obtained.

Example 8

Anhydrous Eye Cream Serum with Additional Ingredients in Base

Ingredients. (1) Butylene Glycol 23.0 (2) Methylpropanediol 26.0 (3) Hydroxypropyl cellulose 0.25 (4) Shea butter (0.5) (5) Murumuru butter 0.5 (6) Ximenia oil 0.5 (7) Coleus oil 0.5 (8) Phenoxyethanol 0.7 (9) Methylpropanediol 30.0 (10) Gluconolactone 5.0 (11) Ascorbic acid 10.0 (12) Resacetophenone 1.5 (13) Titanium Dioxide 1.0 (14) Magnolia Bark Extract 0.2 (15) Matrine 0.2 (16) Ethylhexylglycerin 0.3 (17) Fragrance 0.2. Procedure. Mix (1) to (3) at 80 to 90 C till a clear solution is obtained. Add (4) to (7) with mixing, and cool to 50 to 60 C. Make a premix by mixing (8) to (16) at 50 to 60 C with homogenization to a cream consistency. Add premix to main batch with mixing, then cool to 30 to 40 C and add (17) with mixing. Cool to room temperature.

Example 9

A Method of Treatment of Skin Condition with a Carrier or Base

The method of treatment for skin condition comprises of the following steps; (i) The "complex", according to example 1, is mixed with a suitable carrier, and (II) It is applied on an afflicted area in a sufficient quantity, and, (III) The application is repeated to complete the treatment as desired.

Example 10

A Method of Treatment of Skin Condition with a Delivery System

The method of treatment for skin condition comprises of the following steps;
(i) The "complex", according to example 1, is mixed with a suitable carrier, and
(ii) It is applied on an afflicted area in a sufficient quantity, and,
(iii) The application is repeated to complete the treatment as desired.

Example 11

A Method of Treatment of Skin Condition with the "Complex" Comprising (i) The topical application of said "complex" at a desired site in a sufficient quantity; and, wherein,
(ii) Said application having been done either by a manual or a mechanical method, or a combination thereof; and, wherein
(iii) Said application is repeated to complete the treatment as desired, and, wherein
(iv) Said topical application causes the desired treatment of said skin condition.

Clinical Testing for the Treatment of Skin Condition.

The study was a double blinded, pilot, controlled, single center study. A total of 24 subjects participated in the study. They were divided into two groups of 12 subjects each. Group-A, applied the Serum-A, while the Group-B applied the Serum-B. Each subject was asked to use the given test products on left under-eye for a period of 4 weeks. The right under-eye was the untreated eye. The subjects were assessed on 0 day, and at the end of the $1^{st}$, $2^{nd}$, $3^{rd}$ and the $4^{th}$ week. The assessment was carried out by a Dermatologist for the improvement in the (1) dark circles, (2) puffiness, and (3) wrinkles under the eye. Cutometer readings were taken for the crowfeet area to assess the improvement in skin elasticity. [A detailed description of "Cutometer" has been published: Ahn et al., "Correlation between a Cutometer and quantitative evaluation using Moire topography in age-related skin elasticity", Skin Research and Technology, Volume 13, Number 3, August 2007, pp. 280-284(5).]

Investigational Products.

The investigational products were the two under eye serum formulations and were coded A and B as follows:

Serum-A.

Serum-B.

Serum A. Skin Discoloration and Age Spots Serum Containing In-Situ Generated "Complex" According to [FIG. 1, Formula (I)].

Ingredients. (1) Water 5.0 (2) Ascorbic Acid 5.0 (3) Resacetophenone 2.0 (4) Butylene Glycol 55.0 (5) Diglycerol 20.0 (6) Dow Corning Cosmetic Wax 2501 4.0 (7) Glucono-delta-lactone 5.0 (8) Structure Plus 4.0. Procedure. Ingredients 1 and 2 are mixed and heated at 60 to 65 C till a solution is obtained. Ingredients 3 to 7 are mixed and heated at 60 to 65 C till a solution is obtained. The two solutions are mixed and heated at 60 to 65 C for 30 to 45 minutes, then cooled to 35 to 40 C and ingredient 8 is added with mixing to a desired viscosity. It is cooled to room temperature. A serum-like product is obtained. Glucono-delta-lactone seems to improve stability and increase skin-whitening property of this composition.

Serum B. Skin Whitening and Anti-Wrinkle Serum Containing In-Situ Generated "Complex" According to [FIG. 1, Formula (I)].

Ingredients. (1) Water 5.0 (2) Ascorbic Acid 5.0 (3) Resacetophenone 2.0 (4) Butylene Glycol 60.0 (5) Diglycerol 20.0 (6) Dow Corning Cosmetic Wax 2501 4.0 (7) Structure Plus 4.0. Procedure. Ingredients 1 and 2 are mixed and heated at 60 to 65 C till a solution is obtained. Ingredients 3 to 6 are mixed and heated at 60 to 65 C till a solution is obtained. The two solutions are mixed and heated at 60 to 65 C for 30 to 45 minutes, then cooled to 35 to 40 C and ingredient 7 is added with mixing to a desired viscosity. It is cooled to room temperature. A serum-like product is obtained.

Controls for the Study.

The right under-eye was untreated and that was taken as the control untreated site.

Subject Population.

Total 24 subjects were selected as per the inclusion and exclusion criteria. Inclusion Criteria:

Male and Female (30:70) subjects in generally good health.

Subjects in the age group of 25-45 years.

Subject has not participated in a similar investigation in the past four weeks.

Subjects have not used similar products for the last 4 weeks.

Subjects willing to give a written informed consent and come for regular.

Follow-up.

Subjects should have an under eye puffiness score of 2-3, and under eye dark circle score of 2-3 as mentioned in section 9 of this protocol.

Exclusion Criteria

A Known history or present condition of Allergic response to any cosmetic product.

Subject having skin disease (e.g. psoriasis, atomic dermatitis or other cutaneous manifestations), which would interfere with the test readings.

Subjects having malasma.

Subjects on medications (e.g. steroids or antihistamines), which would compromise the study. The subject is pregnant/nursing.

Duration of Study: Four Weeks.

Study Outline.

Product Application.

The respective test sample was provided to the subjects after the baseline reading. The subjects applied approximately 0.5 grams of the test products on the left under-eye and evenly spread the product gently extending up to the crowfeet region with light strokes till absorbed into the skin. The right under-eye was considered as control or untreated site. The test sample was applied twice daily (i.e. once after bath and second before bedtime) for a period of four weeks on the left under eye region.

Clinical Measurements.

Visual Assessment of Under-eye (By Dermatologist).

The dermatologist graded the both the under-eyes of the subjects on the baseline day and at the end of the $1^{st}$, $2^{nd}$, $3^{rd}$ and $4^{th}$ week as per the following criteria.

(1) Dark circles—The dermatologist graded the under eye dark circles on both the left and right under-eye by using the following scale (half points used when necessary):

| Description | Score |
| --- | --- |
| No dark circles | 0 |
| Mild dark circles | 1 |
| Moderate dark circles | 2 |
| Severe dark circles | 3 |

(2) Puffiness—The dermatologist graded the under eye puffiness on both the left and right under-eye by using the following scale (half points used when necessary):

| Description | Score |
| --- | --- |
| No puffiness | 0 |
| Mild puffiness | 1 |
| Moderate puffiness | 2 |
| Severe puffiness | 3 |

(3) Wrinkles—The dermatologist graded the under eye wrinkles on both the left and right under-eye by using the following scale (half points used when necessary):

| Description | Score |
| --- | --- |
| No wrinkles | 0 |
| Very fine lines | 1 |
| Moderate wrinkles | 2 |
| Deep set wrinkles | 3 |

Instrumental Assessment.

Cutometer: Skin elasticity of both the crowfeet area was recorded using Cutometer.

Results and Statistical Analysis.

Dermatologist's Assessment.

Dark circles.

Serum-A. Compared to the baseline scores, there is a good improvement in the dark circle scores for the treated under-eye. The scores for the untreated under-eye also seem to improve albeit only to a small extent.

Serum-B. Compared to the baseline scores, there is a good improvement in the dark circle scores for the treated under-eye. The scores for the untreated under-eye also seem to improve albeit only to a small extent. However, the differences in improvement between untreated & treated under-eye scores are not statistically significant. 5 of the 12 subjects in the Serum-B group showed significant improvement in the reduction of dark circles.

Serum-A Compared to Serum-B. If the improvements in the scores for the treated under-eye over the improvements in the scores for the untreated under-eye are compared, there is no statistically significant difference between the improvement in dark circles due to Serum-A and Serum-B, although the stability of Serum A is better.

Puffiness.

Serum-A. Compared to the baseline scores, there is a good improvement in the puffiness scores for the treated under-eye. The scores for the untreated under-eye also seem to improve albeit only to a small extent.

Serum-B. Compared to the baseline scores, there is a good improvement in the puffiness scores for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, there is no statistically significant difference between the improvement in puffiness due to Serum-A and Serum-B, although the stability of Serum A is better.

Wrinkles.

Serum-A. Compared to the baseline scores, there is a good improvement in the scores for wrinkles for the treated under-eye. The scores for the untreated under-eye also seem to improve albeit only to a small extent.

Serum-B. Compared to the baseline scores, there is a good improvement in the scores for wrinkles for the treated under-eye. The scores for the untreated under-eye also seem to improve albeit only to a small extent.

Serum-A Compared to Serum-B. If the improvements in the scores for the treated under-eye over the improvements in the scores for the untreated under-eye are compared, Serum-B shows better improvement in reduction of wrinkles post week-3. However the differences are not statistically significant, although the stability of Serum A is better.

Instrumental assessment of Crowfeet area: Cutometer.

Serum-A. Compared to the baseline scores, there is an improvement in the Cutometer readings scores for the treated crowfeet area. Eight of the 11 subjects show significant improvement in Cutometer readings for the treated crowfeet area.

Serum-B. Compared to the baseline scores, there is an improvement in the Cutometer readings scores for the treated crowfeet area. However, the extent of improvement is fluctuating over the four-week period.

Serum-A Compared to Serum-B. There is no statistically significant difference between Serum-A and Serum-B, although the stability of Serum A is better.

Conclusions.

Based on the data it is generally seen that for all the under-eye attributes (dark circle, puffiness, and wrinkles), good amount of improvement is seen after week-3 for both Serum-A and Serum-B, compared to untreated area.

Nutritional Insufficiency.

Ascorbic acid and its derivatives are well known for their vitamin C activity and biological benefits thereof. The ascorbyl complexes of the present invention upon their penetration into dermis release said ascorbyl compound and another skin beneficial compound in accordance to FIG. 1. This provides dual treatment benefits that may have been caused by the nutritional insufficiency of said compounds.

Disfigured Skin.

A combination of dark skin, skin wrinkles and fine lines, and skin puffiness leads to visible disfigured skin. The method of the present invention provides a treatment of all of the above-mentioned ailments, thus providing a relief from disfigured skin.

The invention claimed is:

1. Ascorbyl complex of formula (I), isomers, and salts thereof for oral or topical application:

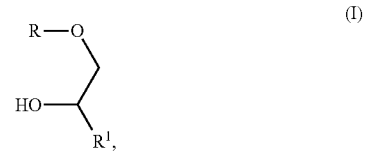

Wherein;
R is selected from H, $C^1$-$C^{20}$ alkyl, aralkyl, and $C^1$-$C^{20}$ acyl;
$R^1$ is selected from the group consisting of:

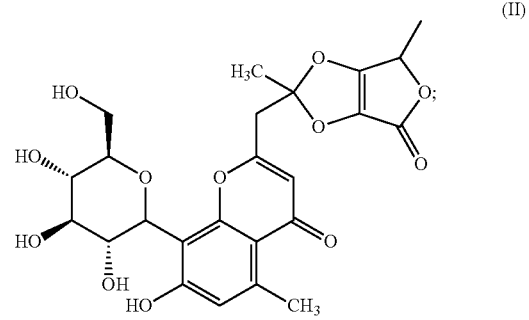

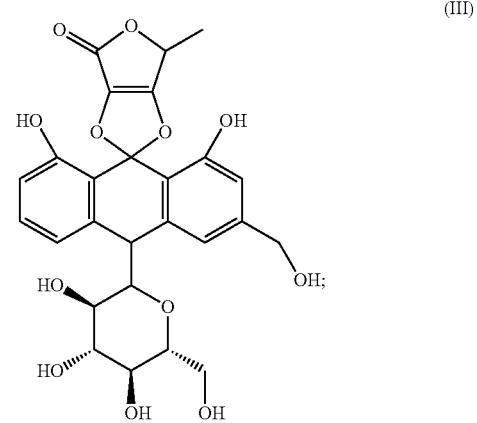

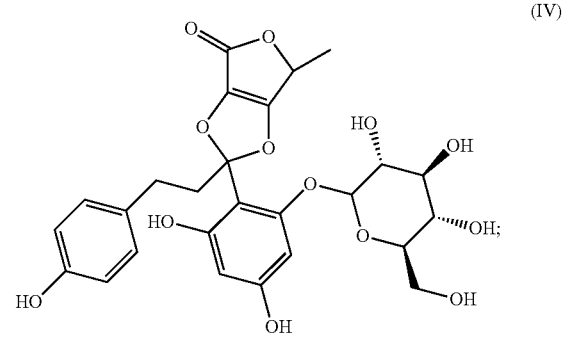

-continued
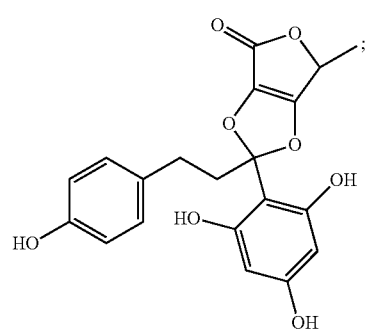
(V)
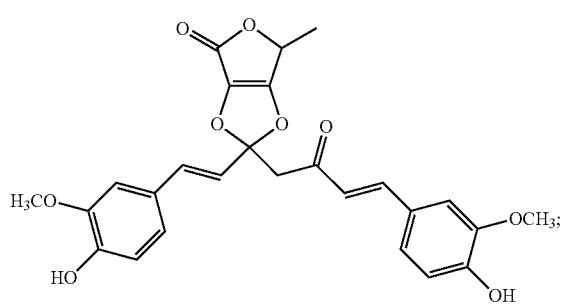
(VI)
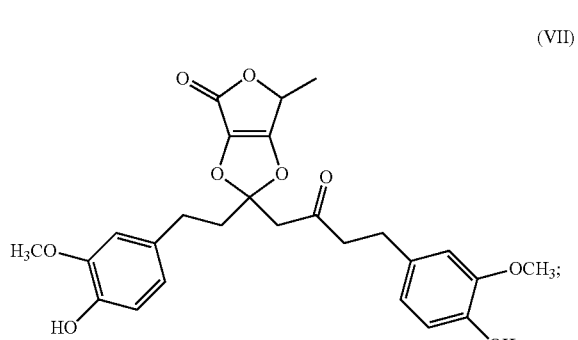
(VII)
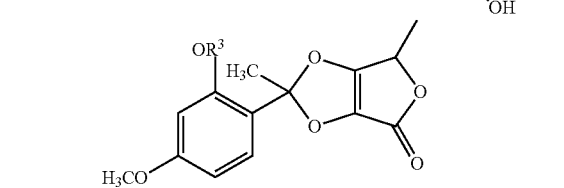
wherein,
R³=H (VIII),
R³=β-D-Glucose (IX);
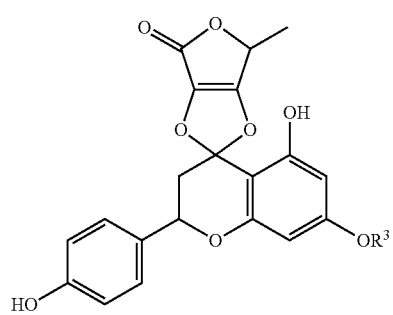
wherein,
R³=H (X),
R³=β-D-Glucose (XI);
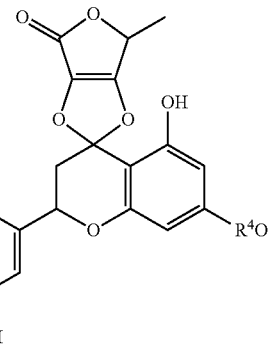
wherein,
R⁴=H (XII),
R⁴=Saccharide (XIII);
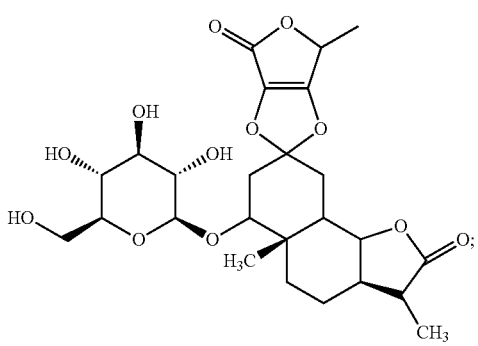
(XIV)
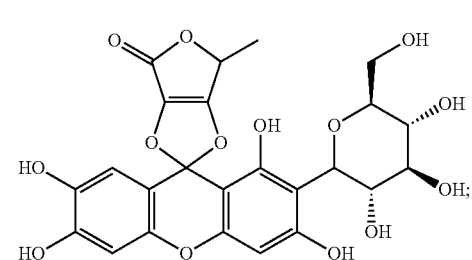
(XV)
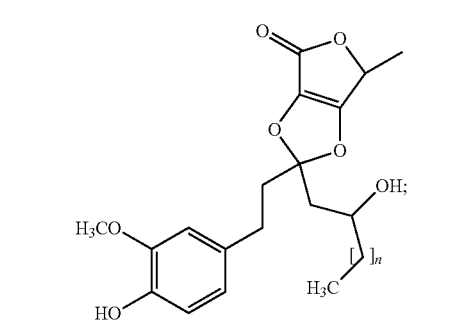
(XVI)
wherein, n=1, 2, 3, 4, 6, 8, 10

(XVII)
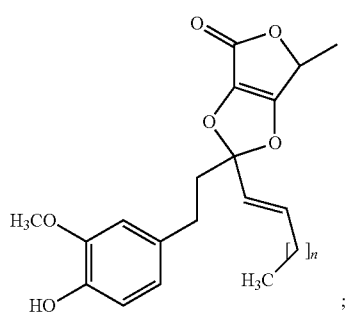
wherein, n=; 3, 4, 5, 6, 8, 10
(XVIII)
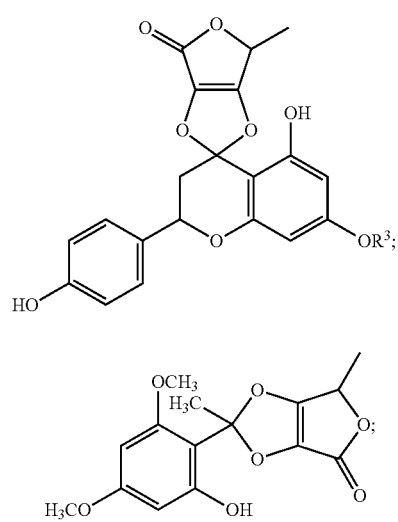
(XIX)
(XX)
(XXI)
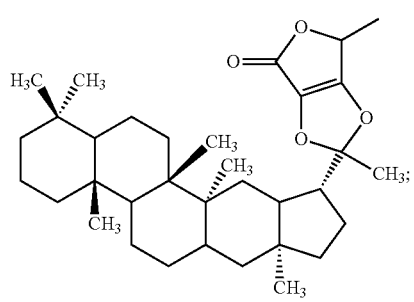
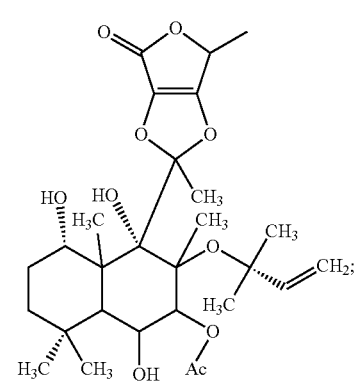
(XXII)
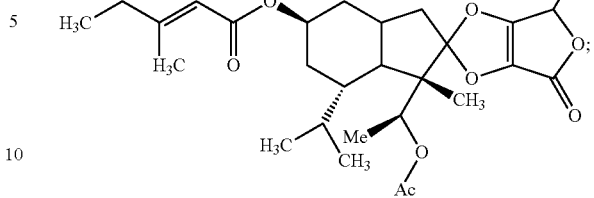
(XXIII)
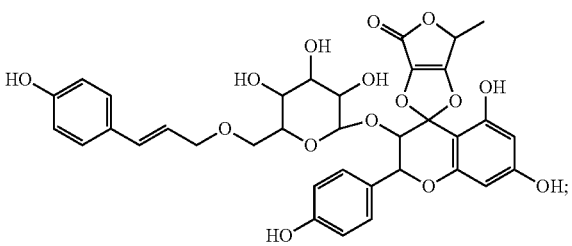
(XXIV)
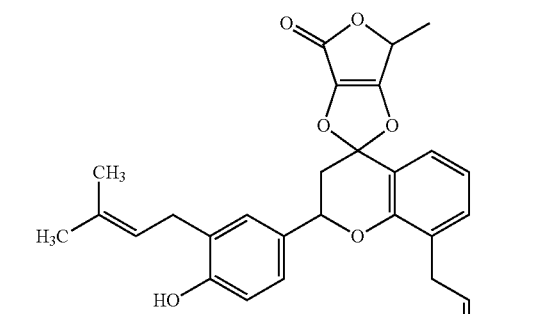
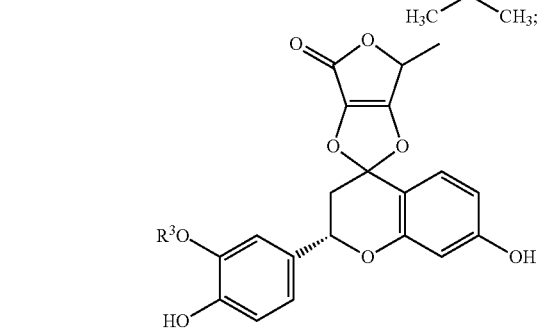
wherein,
R³=H (XXV),
R³=β-D-Glucose (XXVI);
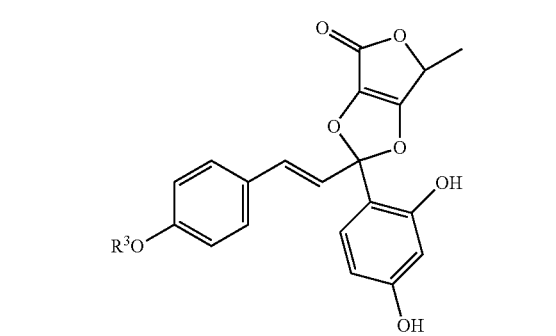

wherein,
R³=H (XXVII)
R³=β-D-Glucose (XXVIII);
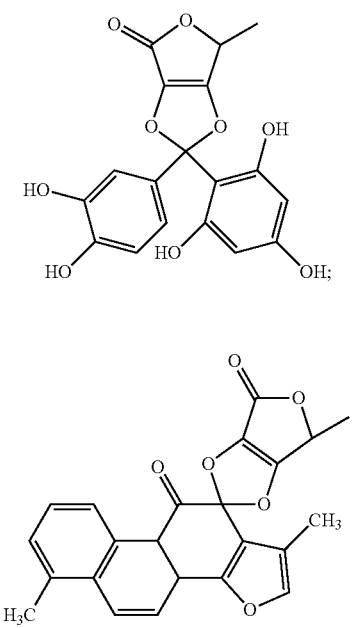
(XXIX)
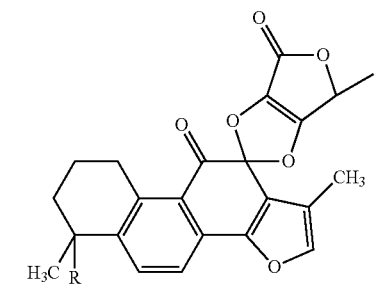
(XXX)
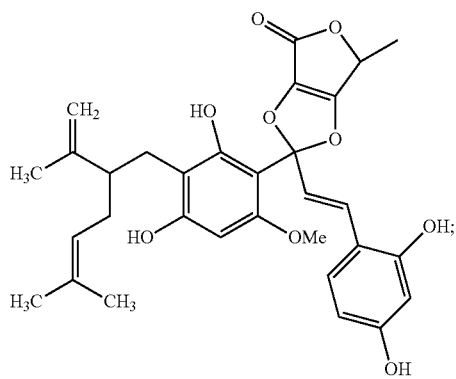
wherein,
R=Me (XXXI),
R=CH₂OH (XXXII);
(XXXIII)
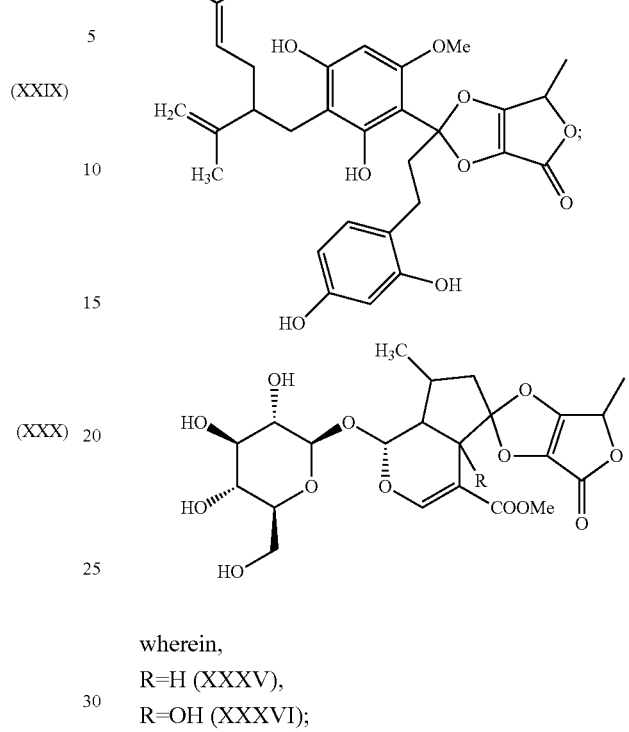
(XXXIV)
wherein,
R=H (XXXV),
R=OH (XXXVI);
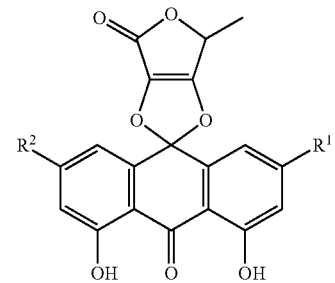
wherein,
R¹=H, R²=CH₃ (XXXVII)
R¹=H, R²=CH₂OH (XXXVIII)
R¹=OH, R²=CH₃ (XXXIX);
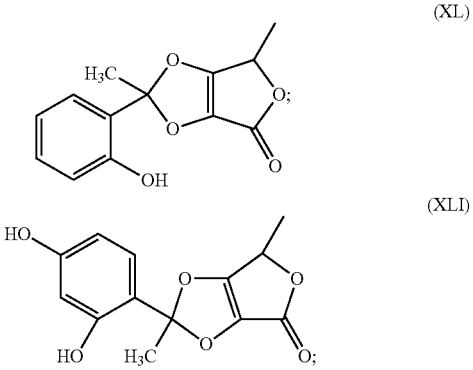
(XL)
(XLI)

(XLII)

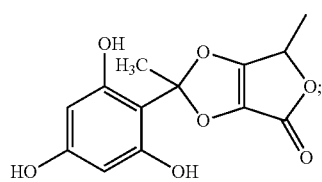

(XLIII)

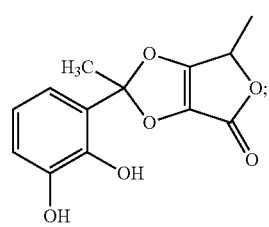

(XLIV)

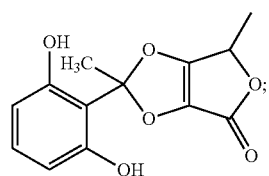

(XLV)

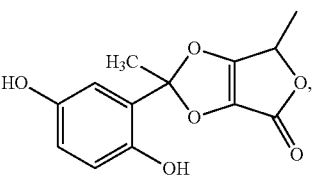

and combinations thereof.

2. A composition comprising ascorbyl complex of claim 1 for oral or topical application.

3. A composition comprising ascorbyl complex of claim 1, wherein said complex is 6-(1,2-dihydroxyethyl)-2-(2,4-dihydroxyphenyl)-2-methyl-furo[3,4-d][1,3]dioxol-4-[6H]-one of formula (XLVI);

(XLVI)

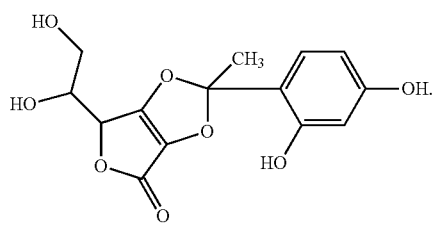

4. A composition comprising ascorbyl complex of claim 1, wherein said complex is 2-[8,9-dihydroxy-2-methyl-7-oxo-1,3,6-trioxaspiro[4,4]non-8-en-2-yl)methyl]-7-hydroxy-5-methyl-8-[(3R,4R,5S,6R)-3,4,5-trihydroxy-6-(hydroxymethyl)tetrahydro-2H-pyran-2-yl]-4H-chromen-4-one of formula (XLVII);

(XLVII)

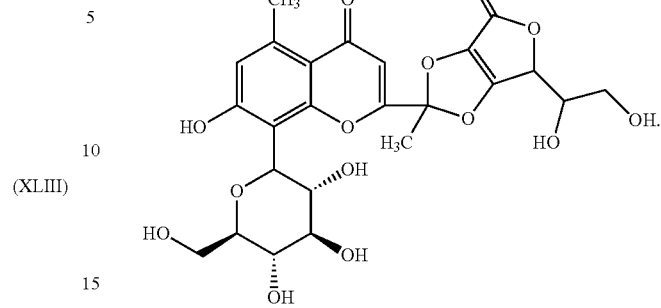

5. A composition comprising ascorbyl complex of claim 1, wherein said isomer complex is 8-(2R,3S,4R,5S)-2-(hydroxymethyl)tetrahydro-2H-pyran-3,4,5-triol-7-hydroxy-2-{[4-hydroxy-4-(hydroxymethyl)-2-methyl-6-oxo-4,6-dihydrofuro[3,4-d][1,3]dioxol-2-yl]methyl}-5-methyl-4H-chromen-4-one of formula (XLVIII) and metal salts thereof;

(XLVIII)

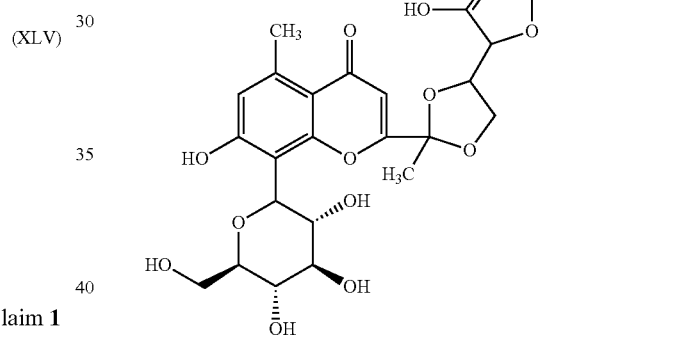

6. A composition comprising the metal salt of an isomer of ascorbyl complex of claim 1, wherein said metal is selected from the group consisting of Li, Na, K, Ti, V, Cr, Mn, Fe, Co, Ni, Cu, Zn and Se.

7. A composition of claim 2 to treat a condition, wherein said condition is selected from the group consisting of dark skin, age spots, acne, rosacea, inflammation, loss of cellular antioxidants, collagen loss, loss of skin pliability, loss of skin suppleness, skin wrinkles, disfigured skin, oxidation, damage from radiation, malfunction of matrix metalloproteases, malfunction of tyrosinases, damage from free radicals, damage from UV, hair loss from malfunction of matrix metalloproteases, hair graying from malfunction of tyrosinases, nutritional insufficiency, and combinations thereof.

8. A composition according to claim 7, wherein said condition is disfigured skin.

9. A composition according to claim 7, wherein said condition is nutritional insufficiency.

10. A method of treatment of skin condition comprising;
(i) The topical application of complex of claim 1, at a desired site in a sufficient quantity; and, wherein,
(ii) Said application having been done either by a manual or a mechanical method, or a combination thereof; and, wherein (iii) Said application is repeated as necessary, and, wherein
(iv) Said application causes the desired treatment of said skin condition.

11. A method according to claim 10, wherein said skin condition is selected from the group consisting of dark skin, age spots, acne, rosacea, inflammation, loss of cellular antioxidants, collagen loss, loss of skin pliability, loss of skin suppleness, skin wrinkles, disfigured skin, oxidation, damage from radiation, malfunction of matrix metalloproteases, malfunction of tyrosinases, damage from free radicals, damage from UV, hair loss from malfunction of matrix metalloproteases, hair graying from malfunction of tyrosinases, nutritional insufficiency, and combinations thereof.

12. A method according to claim 10, wherein said skin condition is disfigured skin.

13. A process for preparing ascorbyl complex of claim 1, which comprises heating of;
(i) An aryl alkyl ketone or a heteroaromatic alkyl ketone; or a plant extract containing the same, and,
(ii) Ascorbic acid or an ascorbic acid derivative, and
(iii) A liquid reaction medium.

\* \* \* \* \*